(12) United States Patent
Sanicola-Nadel et al.

(10) Patent No.: US 7,582,299 B2
(45) Date of Patent: *Sep. 1, 2009

(54) CRIPTO-SPECIFIC ANTIBODIES

(75) Inventors: Michele Sanicola-Nadel, Winchester, MA (US); Heather Adkins, Somerville, MA (US); Steven Donald Miklasz, Upton, MA (US); Paul Rayhorn, Foxboro, MA (US); Susan Gail Schiffer, Lexington, MA (US); Kevin P. Williams, Chapel Hill, NC (US)

(73) Assignee: Biogen Idec MA Inc., Cambridge, MA (US)

( * ) Notice: Subject to any disclaimer, the term of this patent is extended or adjusted under 35 U.S.C. 154(b) by 166 days.

This patent is subject to a terminal disclaimer.

(21) Appl. No.: 10/945,853

(22) Filed: Sep. 20, 2004

(65) Prior Publication Data

US 2005/0255117 A1 Nov. 17, 2005

Related U.S. Application Data

(63) Continuation of application No. PCT/US02/31462, filed on Oct. 1, 2002, which is a continuation of application No. PCT/US02/11950, filed on Apr. 17, 2002.

(60) Provisional application No. 60/286,782, filed on Apr. 26, 2001, provisional application No. 60/293,020, filed on May 17, 2001, provisional application No. 60/301,091, filed on Jun. 26, 2001, provisional application No. 60/367,002, filed on Mar. 22, 2002.

(51) Int. Cl.
*A61K 39/395* (2006.01)
*C07K 16/00* (2006.01)

(52) U.S. Cl. .............. 424/155.1; 424/141.1; 424/130.1

(58) Field of Classification Search .................. None
See application file for complete search history.

(56) References Cited

U.S. PATENT DOCUMENTS

| | | | |
|---|---|---|---|
| 5,208,020 A * | 5/1993 | Chari et al. ............. | 424/181.1 |
| 5,256,643 A | 10/1993 | Persico et al. | |
| 5,264,557 A | 11/1993 | Salomon et al. | |
| 5,530,101 A | 6/1996 | Queen et al. | |
| 5,650,285 A | 7/1997 | Salomon et al. | |
| 5,654,140 A | 8/1997 | Persico et al. | |
| 5,792,616 A | 8/1998 | Persico et al. | |
| 5,854,399 A | 12/1998 | Salomon et al. | |
| 5,981,215 A | 11/1999 | Meissner et al. | |
| 6,207,153 B1 | 3/2001 | Dan et al. | |
| 6,333,410 B1 | 12/2001 | Chari et al. | |
| 6,335,170 B1 | 1/2002 | Orntoft et al. | |
| 6,989,145 B2 | 1/2006 | Shitara et al. | |
| 7,318,924 B2 * | 1/2008 | McKenzie et al. ....... | 424/139.1 |
| 2003/0232755 A1 | 12/2003 | Williams et al. | |
| 2004/0176576 A1 | 9/2004 | McKenzie et al. | |
| 2005/0208045 A1 * | 9/2005 | Vale et al. ................ | 424/143.1 |
| 2005/0255117 A1 | 11/2005 | Sanicola-Nadel et al. | |

FOREIGN PATENT DOCUMENTS

| | | |
|---|---|---|
| JP | 2001-46066 | 2/2001 |
| WO | WO-00/06723 A1 | 2/2000 |
| WO | WO-00/63693 A1 | 10/2000 |
| WO | WO-01/40309 A2 | 6/2001 |
| WO | WO-01/64754 A1 | 9/2001 |
| WO | WO-02/16413 A2 | 2/2002 |
| WO | WO-02/22808 A2 | 3/2002 |
| WO | WO-02/059620 A2 | 8/2002 |
| WO | WO-02/077033 A1 | 10/2002 |
| WO | WO-02/088170 A2 | 11/2002 |
| WO | WO-03/024392 A2 | 3/2003 |
| WO | WO-03/083041 A2 | 10/2003 |
| WO | WO-2006/074397 A2 | 7/2006 |

OTHER PUBLICATIONS

"Structure and Diversity in Three Dimensions," Fundamental Immunology, Third Edition, Ed. W.E. Paul, Raven Press, Chapt. 9, pp. 292-295 (1993).
Qi, C.-F. et al., "Expression of transforming growth factor α, amphiregulin and cripto-1 in human breast carcinomas," *Br. J. Cancer*, vol. 69(5):903-910 (1994).
European Search Report for Application No. 02807155.3—2402, dated Jul. 3, 2006.
Adkins, Heather B. et al, "Antibody blockade of the Cripto CFC domain suppresses tumor cell growth in vivo," *The Journal of Clinical Investigation*, vol. 112(4):575-587 (2003).
Bianco, Caterina, et al., "Cripto-1 Indirectly Stimulates the Tyrosine Phosphorylation of erb B-4 through a Novel Receptor," *The Journal of Biological Chemistry*, vol. 274(13):8624-8629 (1999).
Brandt, Ralf, et al., "Identification and Biological Characterization of an Epidermal Growth Factor-related Protein: Cripto-1," *The Journal of Biological Chemistry*, vol. 269(25):17320-17328 (1994).
Campbell, Ailsa M., "Monoclonal antibody technology," *Laboratory Techniques in Biochemistry and Molecular Biology*, vol. 13, Eds. Burdon, R.H. et al, Elsevier, Amsterdam, New York, Oxford, Chapter 1, pp. 1-32 (1984).
Ciardiello, Fortunato, et al., "Inhibition of Cripto expression and tumorigenicity in human colon cancer cells by antisense RNA and oligodeoxynucleotides," *Oncogene*, vol. 9:291-298 (1994).

(Continued)

*Primary Examiner*—Sheela J Huff
(74) *Attorney, Agent, or Firm*—Lahive & Cockfield, LLP; Megan E. Williams

(57) ABSTRACT

The invention provides Cripto-specific antibodies, or biologically functional fragments thereof, and uses thereof. Antibodies which bind Cripto and inhibit Cripto activity are provided. Antibodies which bind Cripto and inhibit the interaction between Cripto and ALK4 and/or between Cripto and Activin B are provided. Antibodies which bind Cripto and inhibit tumor growth are also provided. Antibodies which bind Cripto, inhibit Cripto activity, and inhibit tumor growth are also provided. The invention also provides methods of using these antibodies in therapeutic, diagnostic, and research applications.

32 Claims, 10 Drawing Sheets

OTHER PUBLICATIONS

Ciccodicola, Alfredo, et al., "Molecular characterization of a gene of the 'EGF family' expressed in undifferentiated human NTERA2 teratocarcinoma cells," *The EMBO Journal*, vol. 8(7):1987-1991 (1989).

Dublin, Edwin A., et al., "amphiregulin and cripto overexpression in breast cancer: relationship with prognosis and clinical and molecular variables," *International Journal of Oncology*, vol. 7:617-622 (1995).

Ebert, Andreas D., et al., "Cripto-1 Induces Phosphatidylinositol 3'-Kinase-dependent Phosphorylation of AKT and Glycogen Synthase Kinase 3β in Human Cervical Carcinoma Cells," *Cancer Research*, vol. 59:4502-4505 (1999).

Hu, X.F. et al, "Cripto monoclonal antibodies," *Drug News Perspect.*, vol. 18(5):293-303 (2005).

Kannan, Subha, et al., "Cripto Enhances the Tyrosine Phosphorylation and Shc and Activates Mitogen-activated Protein Kinase (MAPK) in Mammary Epithelial Cells," *The Journal of Biological Chemistry*, vol. 272(6):3330-3335 (1997).

Normanno, Nicola, et al., "Expression of amphiregulin, cripto-1, and heregulin α in human breast cancer cells," *International Journal of Oncology*, vol. 2:903-911 (1993).

Panico, Luigi et al, "Differential Immunohistochemical Detection of Transforming Growth Factor α, Amphiregulin and Cripto in Human Normal and Malignant Breast Tissue," *Int. J. Cancer*, vol. 65:51-56 (1996).

Saeki, Toshiaki, et al., "Expression of cripto-1 in human colorectal adenomas and carcinomas is related to the degree of dysplasia," *International Journal of Oncology*, vol. 5:445-451 (1994).

Saeki, Toshiaki, et al., "Immunohistochemical detection of cripto-1, amphiregulin and transforming growth factor alpha in human gastric carcinomas and intestinal metaplasias," *International Journal of Oncology*, vol. 5:215-223 (1994).

Salomon, D.S., et al., "The EGF-CFC family: novel epidermal growth factor-related proteins in development and cancer," *Endocrine-Related Cancer*, vol. 7:199-226 (2000).

Schlom, Jeffrey, "Monoclonal Antibodies: They're More and Less Than You Think," *Molecular Foundations of Oncology*, Eds. Broder et al., pp. 95-134 (1991).

International Preliminary Examination Report for Application No. PCT/US02/31462, completed Feb. 7, 2005.

International Search Report for Application No. PCT/US02/31462, dated Oct. 15, 2003.

Ciardiello, Fortunato et al., "Antitumor Activity of Combined Blockade of Epidermal Growth Factor Receptor and Protein Kinase A," *Journal of the National Cancer Institute*, vol. 88(23):1770-1776 (1996).

Dono, Rosanna et al., "Isolation and Characterization of the Cripto Autosomal Gene and Its X-linked Related Sequence," *Am. J. Hum. Genet.*, vol. 49:555-565 (1991).

Friess, Helmut et al., "Cripto, A Member of the Epidermal Growth Factor Family, is Over-expressed in Human Pancreatic Cancer and Chronic Pancratitis," *Int. J. Cancer*, vol. 56:668-674 (1994).

Japanese Office Action for Application No. 2002-585468, dated Nov. 2, 2007.

Schiffer et al., "Fucosylation of Cripto is required for its ability to facilitate Nodal signaling," J. Biol. Chem. vol. 276(41):37769-37778 (2001).

Champier, Jacques et al., "Identification of differentially expressed genes in human pineal parenchymal tumors by microarray analysis," *Acta Neuropathol.*, vol. 109:306-313 (2005).

Hentschke, Moritz et al., "Germ Cell Nuclear Factor Is a Repressor of Cripto-1 and Cripto-3," *The Journal of Biological Chemistry*, vol. 281(44):33497-33504 (2006).

Hu, X.F. et al., "Anti-Cripto Mab inhibit tumour growth and overcome MDR in a human leukaemia MDR cell line by inhibition of Akt and activation of JNK/SAPK and bad death pathways," *British Journal of Cancer*, vol. 96:918-927 (2007).

LePage, Doreen J. et al., "Inhibition of human tumor xenografts by anti-Cripto antibodies," *Proceedings of the American Association for Cancer Research*, vol. 44, 2nd Ed., p. 145, No. 749 (2003).

Rudikoff, Stuart et al., "Single amino acid substitution altering antigen-binding specificity," *Proc. Natl. Acad. Sci. USA*, vol. 79:1979-1983 (1982).

Sugino, Yukio, "Biotechnology Series, Monoclonal Antibody." 1986, pp. 1-22.

Welss, Thomas et al., "Molecular basis of basal cell carcinoma: Analysis of differential gene expression by differential display PCR and expression array," *Int. J. Cancer*, vol. 104:66-72 (2003).

Xing, Pei Xiang et al., "Cripto: A Novel Target for Antibody-Based Cancer Immunotherapy," *Cancer Research*, vol. 64:4018-4023 (2004).

* cited by examiner

CRIPTO-SPECIFIC ANTIBODIES

RELATED APPLICATIONS

This application is a Continuation of PCT/US02/31462, filed Oct. 1, 2002, which application is a Continuation-in-part of PCT/US02/11950, filed Apr. 17, 2002, which application claimed the benefit of U.S. Ser. No. 60/367,002, filed Mar. 22, 2002; U.S. Ser. No. 60/301,091, filed Jun. 26, 2001; U.S. Ser. No. 60/293,020, filed May 17, 2001; and U.S. Ser. No. 60/286,782, filed Apr. 26, 2001. The entire disclosure of each of the aforesaid patent applications is incorporated herein by reference.

TECHNICAL FIELD OF THE INVENTION

This invention relates generally to the fields of genetics and cellular and molecular biology. More particularly, the invention relates to anti-Cripto antibodies.

BACKGROUND OF THE INVENTION

Cripto is a 188-amino-acid cell surface protein. It was serendipitously isolated in a cDNA screen of a human embryonic carcinoma library (Ciccodicola et al., 1989, *EMBO J.* 8:1987-91). The Cripto protein has at least two notable domains: a cysteine-rich (cys-rich) domain, and a domain first characterized as similar to the domain found in the epidermal growth factor (EGF) family. Cripto was originally classified as a member of the EGF family (Ciccodicola et al., supra); however, subsequent analysis showed that Cripto did not bind any of the known EGF receptors and its EGF-like domain was actually divergent from the EGF family (Bianco et al., 1999, *J. Biol. Chem.* 274:8624-29).

The Cripto signaling pathway has remained elusive despite continued investigation. The literature supports activation of several different pathways, including a MAP kinase pathway (DeSantis et al., 1997, *Cell Growth Differ.* 8:1257-66; Kannan et al., 1997, *J. Biol. Chem.* 272:3330-35); the TGF-β pathway (Gritsman et al., 1999, *Development* 127:921-32; Schier et al., 2000, *Nature* 403:385-89); possible interactions with the Wnt pathway (Salomon et al., 2000, *Endocr. Relat. Cancer.* 7:199-226); and cross-talk with the EGF pathway (Bianco et al., 1999, *J. Biol. Chem.* 274:8624-29).

U.S. Pat. No. 5,256,643 and two patents related thereto (U.S. Pat. Nos. 5,654,140 and 5,792,616) disclose a human Cripto gene, the Cripto protein, and antibodies to Cripto.

U.S. Pat. No. 5,264,557 and three patents related thereto (U.S. Pat. Nos. 5,620,866, 5,650,285, and 5,854,399) disclose a human Cripto-related gene and protein. Also disclosed are antibodies which bind to the Cripto-related protein but do not cross react by binding to the Cripto protein itself.

Overexpression of the Cripto protein is associated with tumors in many tissues (including, but not limited to brain, breast, testicular, colon, lung, ovary, bladder, uterine, cervical, pancreatic and stomach), as demonstrated by immunostaining of human tissue with rabbit polyclonal antibodies raised against small Cripto peptides. Panico et al., 1996, *Int. J. Cancer* 65:51-56; Byrne et al., 1998, *J. Pathology* 185:108-11; De Angelis et al., 1999, *Int. J. Oncology* 14:437-40. The art is therefore in need of means of controlling, restricting, and/or preventing such overexpression, inhibiting Cripto activity, and inhibiting the consequences of Cripto expression (i.e., promotion and/or maintenance of cell transformation).

SUMMARY OF THE INVENTION

This invention provides novel antibodies which specifically bind to Cripto, and methods of making and using such antibodies. The invention also provides antibodies which bind to Cripto, and inhibit Cripto activity or protein interaction, e.g., an antibody which binds to Cripto such that the signal resulting from a protein interaction with Cripto is modulated downward. The invention also provides antibodies which bind to Cripto and block the interaction between Cripto and ALK4. The invention also provides antibodies which bind to Cripto and block the interaction between Cripto and Activin B. The invention also provides antibodies which bind to Cripto and inhibit tumor growth. The invention also provides antibodies which bind to Cripto, inhibit Cripto activity and inhibit tumor growth. The invention also provides antibodies which bind to Cripto, block the interaction between Cripto and ALK4 and/or between Cripto and Activin B, and inhibit tumor growth.

In one aspect of the invention, the antibody of the invention specifically binds to an epitope selected from the group of epitopes to which antibodies A6C12.11, A6F8.6 (ATCC ACCESSION NO. PTA-3318), A7H1.19, A8F1.30, A8G3.5 (ATCC ACCESSION NO. PTA-3317), A8H3.1 (ATCC ACCESSION NO. PTA-3315), A8H3.2, A10A10.30, A19A10.30, A10B2.17, A10B2.18 (ATCC ACCESSION NO. PTA-3311), A27F6.1 (ATCC ACCESSION NO. PTA-3310), A40G12.8 (ATCC ACCESSION NO. PTA-3316), A2D3.23, A7A10.29, A9G9.9, A15C12.10, A15E4.14, A17A2.16, A17C12.28, A17G12.1 (ATCC ACCESSION NO. PTA-3314), A17H6.1, A18B3.11 (ATCC ACCESSION NO. PTA-3312), A19E2.7, B3F6.17 (ATCC ACCESSION NO. PTA-3319), B6G7.10 (ATCC ACCESSION NO. PTA-3313), 1-1A4C.2, 2-2C9.2, 2-3H9.2, 2-4E5.6, 2-4D1.3, 3-4E8.3, 3-3G1.1, 4-2F6, 4-3A7 and 4-1E2 bind.

In another aspect of the invention, the antibody of the invention specifically binds to an epitope in the ligand/receptor binding domain of Cripto. Cripto can be selected from CR-1 (SEQ ID NO:1) or CR-3 (SEQ ID NO: 2). In a more particular embodiment, antibodies that specifically bind to the epitope in the ligand/receptor binding domain include, for example, A6C12.11, A6F8.6 (ATCC ACCESSION NO. PTA-3318), A7H1.19, A8F1.30, A8G3.5 (ATCC ACCESSION NO. PTA-3317), A8H3.1 (ATCC ACCESSION NO. PTA-3315), A8H3.2, A10A10.30, A19A10.30, A10B2.17, A10B2.18 (ATCC ACCESSION NO. PTA-3311), A27F6.1 (ATCC ACCESSION NO. PTA-3310), A40G12.8 (ATCC ACCESSION NO. PTA-3316), A2D3.23, A7A10.29, A9G9.9, A15C12.10, A15E4.14, A17A2.16, A17C12.28, A17G12.1 (ATCC ACCESSION NO. PTA-3314), A17H6.1, A18B3.11 (ATCC ACCESSION NO. PTA-3312), A19E2.7, B3F6.17 (ATCC ACCESSION NO. PTA-3319), B6G7.10 (ATCC ACCESSION NO. PTA-3313), 1-1A4C.2, 2-2C9.2, 2-3H9.2, 2-4E5.6, 2-4D1.3, 3-4E8.3, 3-3G1.1, 4-2F6, 4-3A7 and 4-1E2.

In some embodiments, the epitope to which the antibodies of the invention bind is in an EGF-like domain. Antibodies that specifically bind to an epitope in the EGF-like domain include, but are not limited to, A40G12.8 (ATCC ACCESSION NO. PTA-3316), A8H3.1 (ATCC ACCESSION NO. PTA-3315), A27F6.1 (ATCC ACCESSION NO. PTA-3310), B6G7.10 (ATCC ACCESSION NO. PTA-3313), A17G12.1

(ATCC ACCESSION NO. PTA-3314), A18B3.11 (ATCC ACCESSION NO. PTA-3312), 1-1A4C.2, 2-2C9.2 and 2-4D1.3.

In other embodiments the epitope to which the antibodies of the invention bind is in a cys-rich domain. Antibodies that specifically bind to an epitope in the cys-rich domain include, but are not limited to, A19A10.30, A8G3.5 (ATCC ACCESSION NO. PTA-3317), A6F8.6 (ATCC ACCESSION NO. PTA-3318), A6C12.11, 1-1A4C.2 and 2-2C9.2.

In still other embodiments the epitope to which the antibodies of the invention bind is in the amino terminus. Antibodies that specifically bind to an epitope in the amino terminus include, but are not limited to, A10B2.17.

In still other embodiments the epitope to which the antibodies of the invention bind is in the domain spanning amino acid residues 46-62 of Cripto. Antibodies that specifically bind to the epitope in the domain spanning amino acid residues 46-62 of Cripto include, but are not limited to, A10B2.18 (ATCC ACCESSION NO. PTA-3311), B3F6.17 (ATCC ACCESSION NO. PTA-3319), A17A2.16, 2-3H9.2, 2-4E5.6, 2-4D1.3, 3-4E8.3, 3-1E7.2 and 3-3G1.1.

In other embodiments the epitope to which the antibodies of the invention bind is in the CR40 (SEQ ID NO: 3), CR41 (SEQ ID NO: 4), CR43 (SEQ ID NO: 5), CR44 (SEQ ID NO: 6), CR49 (SEQ ID NO: 7), CR50 (SEQ ID NO: 8) or CR51 (SEQ ID NO: 9) polypeptides. Antibodies that specifically bind to an epitope in one of these polypeptides include, but are not limited to, A6C12.11, A6F8.6, A7H1.19, A8F1.30, A8G3.5, A8H3.1, A8H3.2, A10A10.30, A19A10.30, A10B2.17, A10B2.18, A27F6.1, A40G12.8, A2D3.23, A7A10.29, A9G9.9, A15C12.10, A15E4.14, A17A2.16, A17C12.28, A17G12.1, A17H6.1, A18B3.11, A19E2.7, B3F6.17, B6G7.10, 1-1A4C.2, 2-2C9.2, 2-3H9.2, 2-4E5.6, 2-4D1.3, 3-4E8.3, 3-3G1.1, 4-2F6, 4-3A7 and 4-1E2.

This invention also includes antibodies which bind specifically to Cripto and are capable of inhibiting Cripto activity. Antibodies that bind specifically to Cripto and are capable of inhibiting Cripto activity include, but are not limited to, A40G12.8 (ATCC ACCESSION NO. PTA-3316), A8H3.1 (ATCC ACCESSION NO. PTA-3315), A27F6.1 (ATCC ACCESSION NO. PTA-3310), A6C12.11, 1-1A4C.2 and 2-2C9.2. In some embodiments, the antibodies of the invention which bind specifically to Cripto and are capable of inhibiting Cripto activity bind to an epitope in an EGF-like domain or a cys-rich domain of Cripto.

This invention also includes antibodies which bind specifically to Cripto and block the interaction between Cripto and ALK4. Antibodies that bind specifically to Cripto and are capable of blocking the interaction between Cripto and ALK4, include but are not limited to, A8G3.5 (ATCC ACCESSION NO. PTA-3317), A6F8.6 (ATCC ACCESSION NO. PTA-3318), A6C12.11, 1-1A4C.2 and 2-2C9.2. In some embodiments, the antibodies of the invention which bind specifically to Cripto and are capable of blocking the interaction between Cripto and ALK4 bind to an epitope in an EGF-like domain or a cys-rich domain of Cripto.

This invention also includes antibodies which bind specifically to Cripto and block the interaction between Cripto and Activin B. Antibodies that bind specifically to Cripto and are capable of blocking the interaction between Cripto and Activin B, include but are not limited to, A8G3.5 (ATCC ACCESSION NO. PTA-3317) and 1-1A4C.2. In some embodiments, the antibodies of the invention which bind specifically to Cripto and are capable of blocking the interaction between Cripto and Activin B bind to an epitope in a cys-rich domain of Cripto.

In another aspect, this invention includes antibodies which bind specifically to Cripto and are capable of inhibiting tumor growth. Antibodies that specifically bind to Cripto and are capable of inhibiting tumor growth include, but are not limited to, A27F6.1 (ATCC ACCESSION NO. PTA-3310), B6G7.10 (ATCC ACCESSION NO. PTA-3313) and A8G3.5 (ATCC ACCESSION NO. PTA-3317), 1-1A4C.2 and 2-2C9.2.

In some embodiments, the antibodies of the invention which bind specifically to Cripto and are capable of inhibiting tumor growth bind to an epitope in an EGF-like domain or a cys-rich domain of Cripto.

In yet another aspect, this invention includes antibodies which bind specifically to Cripto, which are capable of inhibiting Cripto activity, and which are capable of inhibiting tumor growth. Antibodies that specifically bind to Cripto, which are capable of inhibiting Cripto activity, and which are capable of inhibiting tumor growth include, but are not limited to, A27F6.1 (ATCC ACCESSION NO. PTA-3310), A8G3.5, 1-1A4C.2 and 2-2C9.2.

In some embodiments, the antibodies of this invention which bind specifically to Cripto, which are capable of inhibiting Cripto activity, and which are capable of inhibiting tumor growth bind to an epitope in an EGF-like domain or a cys-rich domain of Cripto.

In yet another aspect, this invention includes antibodies which bind specifically to Cripto, which are capable of blocking the interaction between Cripto and ALK4, and which are capable of inhibiting tumor growth. Antibodies that specifically bind to Cripto, which are capable of blocking the interaction between Cripto and ALK4, and which are capable of inhibiting tumor growth include, but are not limited to, A8G3.5 (ATCC ACCESSION NO. PTA-3317), 1-1A4C.2 and 2-2C9.2.

In yet another aspect, this invention includes antibodies which bind specifically to Cripto, which are capable of blocking the interaction between Cripto and Activin B, and which are capable of inhibiting tumor growth. Antibodies that specifically bind to Cripto, which are capable of blocking the interaction between Cripto and Activin B, and which are capable of inhibiting tumor growth include, but are not limited to, A8G3.5 (ATCC ACCESSION NO. PTA-3317) and 1-1A4C.2.

In another aspect, the invention includes a method for inhibiting binding of Cripto to Activin B in a sample, comprising adding to the sample an antibody that binds specifically to Cripto and which is capable of blocking the interaction between Cripto and Activin B. In a related aspect, the invention includes a method for inhibiting binding of Cripto to Activin B in a mammal, comprising administering to the mammal an antibody which binds specifically to Cripto and which is capable of blocking the interaction between Cripto and Activin B.

In another embodiment, the invention provides an antibody produced by a hybridoma selected from the group consisting of A6F8.6 (ATCC Accession No. PTA-3318), A8G3.5 (ATCC Accession No. PTA-3317), A8H3.1 (ATCC Accession No. PTA-3315), A10B2.18 (ATCC Accession No. PTA-3311), A27F6.1 (ATCC Accession No. PTA-3310), A40G12.8 (ATCC Accession No. PTA-3316), A17G12.1 (ATCC Accession No. PTA-3314), A18B3.11 (ATCC Accession No. PTA-3312), B3F6.17 (ATCC Accession No. PTA-3319), B6G7.10 (ATCC Accession No. PTA-3313), 1-1A4C.2, 2-2C9.2, 2-3H9.2, 2-4E5.6, 2-4D1.3, 3-4E8.3, 3-3G1.1, 4-2F6, 4-3A7 and 4-1E2. Several of the antibodies have alternative designations as follows: 1-1A4C.2 is the same as 1P1A4-C2.1 (ATCC Accession No. to be assigned);

2-2C9.2 is the same as 2P2C9.2 (ATCC Accession No. to be assigned); 2-4E5.6 is the same as 2P4E5.6 (ATCC Accession No. to be assigned); 3-3G1.1 is the same as 3P3G1.1 (ATCC Accession No. to be assigned); and 3-4E8.3 is the same as 3P4E8.3 (ATCC Accession No. to be assigned).

The antibodies of the invention include, but are not limited to, monoclonal, polyclonal, humanized, chimeric and human antibodies.

This invention also provides a composition for administration to a mammal having a tumor that expresses Cripto comprising at least one of the antibodies described above. In some embodiments, the mammal is human. The composition may include a pharmaceutically acceptable excipient. The antibodies described above can be conjugated to a chemotherapeutic agent or can be provided in combination with a nonconjugated chemotherapeutic.

Included in another aspect of the invention are methods of inhibiting growth of tumor cells in vitro in a sample comprising the step of adding to the sample a composition described above.

Also included are methods of inhibiting growth of tumor cells in vivo in a mammal comprising the step of administering to the mammal an effective amount of a composition described above. In some embodiments the mammal is human.

Another aspect of the invention is a method of treating a mammal having a tumor that overexpresses Cripto comprising administering to the mammal a composition described above in an effective amount. A composition for administration may include pharmaceutically acceptable excipients, antibodies conjugated to chemotherapeutic agents and antibodies administered in combination with nonconjugated chemotherapeutic agents.

The methods of the invention are particularly useful in inhibiting growth of tumor cells and/or treating a mammal (e.g., a human) having a tumor where the tumor cell is selected from brain, breast, testicular, colon, lung, ovary, bladder, uterine, cervical, pancreatic and stomach tumor cells.

In yet another embodiment, the invention includes methods of determining whether a tissue expresses Cripto, comprising the step of analyzing tissue from the mammal in an immunoassay using any of the antibodies described above. Also included are methods of determining whether a cell line overexpresses Cripto, comprising the step of analyzing the cell line in an immunoassay using any of the antibodies described above.

In a further aspect, the invention provides a method of preserving or maintaining Activin B-induced inhibition of a tumor cell, comprising exposing the tumor cell to an antibody of the invention. In certain embodiments, the tumor cell is a human tumor cell. In some embodiments the tumor cell is selected from brain, breast, testicular, colon, lung, ovary, bladder, uterine, cervical, pancreatic and stomach tumor cells.

In still another aspect, the invention provides a method for identifying a compound which is capable of blocking the interaction between Cripto and Activin B, comprising the steps of contacting Cripto and Activin B in the presence of a candidate compound and detecting a change the interaction between Cripto and Activin B. In some embodiments the compound is an antibody.

These and other aspects of the invention are set forth in greater detail below in the Detailed Description of the Invention

DETAILED DESCRIPTION OF THE INVENTION

Figure 1:
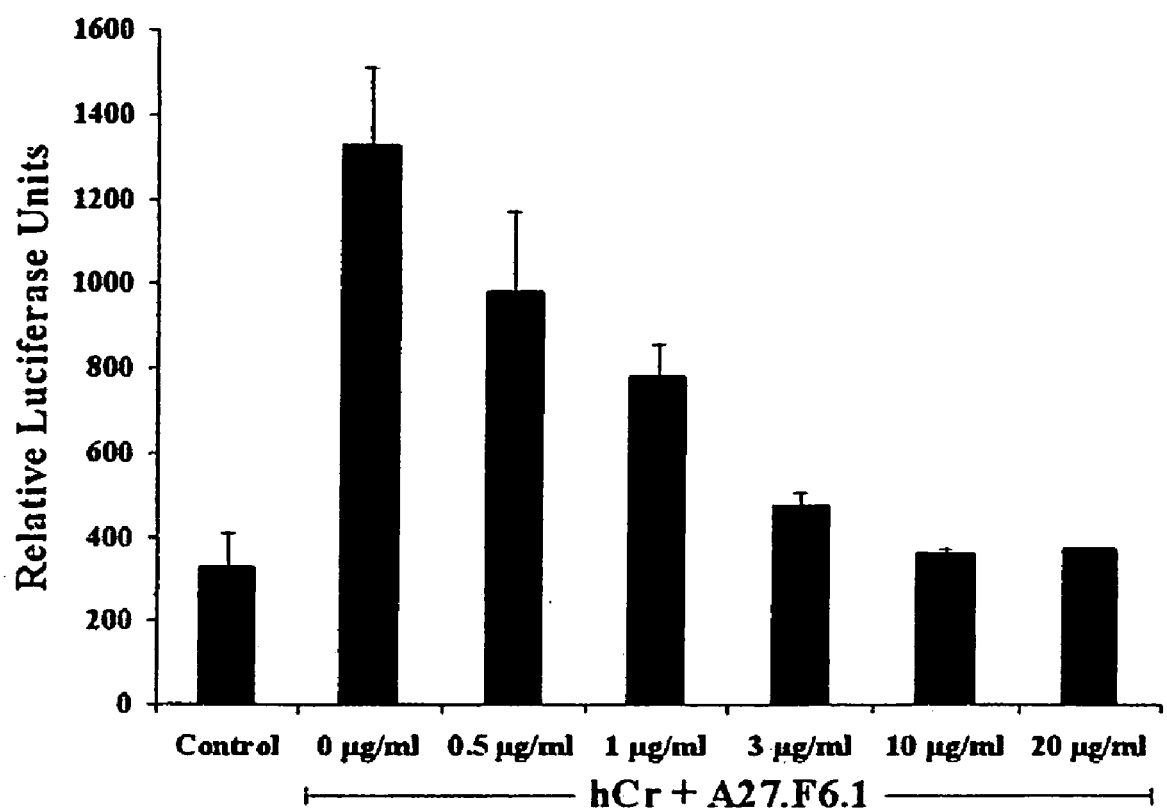
FIG. 1 shows that the addition of 0.5-20 mg/ml mab A27F6.1 to the media of cells inhibited the Cripto-induced luciferase signal by 34-95%.

This invention is based on the discovery that certain Cripto-specific antibodies can affect Cripto activity by, e.g., inhibiting the interaction between Cripto and ALK4 and/or the interaction between Cripto and Activin B, and can be used to inhibit the growth of tumor cells. Some of these antibodies specifically bind to an epitope in the ligand/receptor binding domain of either a native Cripto protein or a denatured form of Cripto. For instance, they may bind to an EGF-like domain, a cys-rich domain, or a peptide (e.g., from about 3 to about 20 amino acids) from the region spanning amino acid residues 46 to 150 of Cripto.

The antibodies of this invention are useful in the therapy of malignant or benign tumors of mammals where the growth of the tumor is at least partially dependent upon Cripto. This growth usually has an abnormal growth rate that is in excess of that required for normal homeostasis and is in excess of that for normal tissues of the same origin.

I. Definitions

Various definitions are made throughout this document. Most words have the meaning that would be attributed to those words by one skilled in the art. Words specifically defined either below or elsewhere in this document have the meaning provided in the context of the invention as a whole and are as typically understood by those skilled in the art.

As used herein, "region" means a physically contiguous portion of the primary structure of a biomolecule. In the case of proteins, a region is defined by a contiguous portion of the amino acid sequence of that protein.

As used herein, "domain" means a structural part of a biomolecule that contributes to a known or suspected function of the biomolecule. Domains may be co-extensive with regions or portions thereof; domains may also incorporate a portion of a biomolecule that is distinct from a particular region, in addition to all or part of that region. Examples of protein domains include, but are not limited to, the extracellular domain (spans from about residue 31 to about residue 188 of Cripto, including CR-1 (SEQ ID NO:1) and CR-3 (SEQ ID NO:2)) and the transmembrane domain (spans from about residue 169 to about residue 188 of Cripto, including CR-1 and CR-3). A ligand/receptor binding domain of the Cripto protein spans from about residue 75 to about residue 150 of Cripto, including CR-1 and CR-3; this domain includes the EGF-like domain, which spans, for example, from about residue 75 to about residue 112 of Cripto, including CR-1 and CR-3, and the cys-rich domain, which spans, for example, from about residue 114 to about residue 150 of Cripto, including CR-1 and CR-3. Many monoclonal antibodies of the invention were identified as binding to the EGF-like or cys-rich domain. Additionally, monoclonal antibodies A10B2.18 (ATCC ACCESSION NO. PTA-3311), B3F6.17 (ATCC ACCESSION NO. PTA-3319) and A17A2.16 have been identified as binding to an epitope formed in a domain in the region spanning amino acid residues 46-62 of Cripto upstream of the EGF-like domain. See Example 3 below.

An epitope to which an anti-Cripto antibody of the invention binds may be present in the conformationally native Cripto protein or the denatured Cripto protein. In addition, an epitope can be formed by noncontiguous sequences in the Cripto polypeptide.

As used herein, an antibody of this invention can be, for instance, a murine antibody, a humanized antibody, a fully human antibody, or a chimeric antibody. It can be a whole antibody (i.e., with two full length light chains and two full length heavy chains) of any isotype and subtypes (e.g., IgM, IgD, IgG1, IgG2, IgG3, IgG4, IgE, IgA1 and IgA2; with either kappa or lambda light chain). Alternatively, the antibody of this invention refers to an antigen-binding fragment (e.g., Fab, F(ab')2, and single chain Fv) of a whole antibody.

Any of the antibodies of the invention may optionally be conjugated to a chemotherapeutic, as defined below.

As used herein, "an antibody capable of internalizing Cripto" means an antibody which enters the cell while removing Cripto from the cell surface. One can screen for Cripto antibodies which are capable of internalizing Cripto by, for example, using fluorescently labeled Cripto monoclonal antibodies. In order to determine which antibodies can be internalized into the Cripto positive cells one can assay for the uptake of the fluorescent signal of the labeled antibodies into the cells by viewing the cells under a fluorescent and/or confocal microscope. Those antibodies that are internalized will be seen as fluorescent signals in the cytoplasmic and/or cellular vesicles. Non-limiting examples of Cripto antibodies capable of internalizing Cripto include A27F6.1, B3F6.17 and 1-1A4C.2.

As used herein, "compound" means any identifiable chemical or molecule, including, but not limited to, ion, atom, small molecule, peptide, protein, sugar, nucleotide, and nucleic acid. Such a compound can be natural or synthetic.

As used herein, "modulate" or "modify" means an increase or decrease in the amount, quality, or effect of a particular activity or protein.

As used herein, "inhibit" means a decrease in the amount, quality or effect of a particular activity or protein.

As used herein, "modulate Cripto activity" means an increase or decrease in the amount, quality, or effect of Cripto activity. The increase or decrease in the amount, quality, or effect of Cripto activity can be by at least about, for example, 5%, 10%, 20%, 30%, 40%, 50%, 60%, 70%, 80%, 90%, or 100%. Increases greater than about 100% are also envisioned, for example, at least about 3, 4, 5, 10, 20 or more fold. Activity may be measured by assays known in the art, such as the null cell assay shown in Example 3. In some embodiments, protein interaction between Cripto and another protein is inhibited via binding of the antibodies of the invention.

As used herein, "blocking the interaction between Cripto and ALK 4" or "modulating the interaction between Cripto and ALK 4" means an increase or decrease in the interaction, i.e. binding, between Cripto and ALK4. The increase or decrease in the interaction can be by at least about, for example, 5%, 10%, 20%, 30%, 40%, 50%, 60%, 70%, 80%, 90%, or 100%. Increases greater than about 100% are also envisioned, for example, about 3, 4, 5, 10, 20 or more fold. Activity may be measured by assays known in the art, such as the binding assay shown in Example 8.

As used herein, "blocking the interaction between Cripto and Activin B" or "modulating the interaction between Cripto and Activin B" means an increase or decrease in the interaction, i.e. binding, between Cripto and Activin B. The increase or decrease in the interaction can be by at least about, for example, 5%, 10%, 20%, 30%, 40%, 50%, 60%, 70%, 80%, 90%, or 100%. Increases greater than about 100% are also envisioned, for example, about 3, 4, 5, 10, 20 or more fold. Activity may be measured by assays known in the art, such as the binding assay shown in Example 11

As used herein, "modulate growth of tumor cells in vitro" means an increase or decrease in the number of tumor cells in vitro. The increase or decrease in the number of tumor cells can be by at least about, for example, 5%, 10%, 20%, 30%, 40%, 50%, 60%, 70%, 80%, 90%, or 100%. Increases greater than about 100% are also envisioned, for example, about 3, 4, 5, 10, 20 or more fold. In vitro modulation of tumor cell growth may be measured by assays known in the art, such as the GEO cell soft agar assay shown in Example 4.

As used herein, modulate growth of tumor angiogenesis, and/or metastasis of tumor cells in vivo. The decrease in the number of tumor cells can be by at least about, for example, 5%, 10%, 20%, 30%, 40%, 50%, 60%, 70%, 80%, 90%, or 100%. In vivo modulation of tumor cell growth may be measured by assays known in the art, such as the one shown in Example 5.

As used herein, "therapeutic effect" means the inhibition of an abnormal condition. A therapeutic effect relieves to some extent one or more of the symptoms of the abnormal condition. In reference to the treatment of abnormal conditions, a therapeutic effect can refer to one or more of the following: (a) an increase or decrease in the proliferation, growth, and/or differentiation of cells; (b) inhibition (i.e., slowing or stopping) or promotion (i.e., increasing or starting) of cell death; (c) inhibition of degeneration; (d) relieving to some extent one or more of the symptoms associated with the abnormal condition; and (e) enhancing the function of a population of cells. Compounds demonstrating efficacy against abnormal conditions can be identified as described herein.

As used herein, "administering" means a method of incorporating a compound into cells or tissues of an organism. The abnormal condition can be prevented or treated when the cells or tissues of the organism exist within the organism (in vivo) or outside of the organism (ex vivo). Cells existing outside the organism can be maintained or grown in cell culture dishes, or in another organism. For cells harbored within the organism, many techniques exist in the art to administer compounds, including (but not limited to) oral, parenteral, dermal, injection, and aerosol applications. For cells outside of the organism, multiple techniques exist in the art to administer the compounds, including (but not limited to) cell microinjection techniques, transformation techniques and carrier techniques. Administration may be accomplished by the many modes known in the art, e.g., oral, intravenous, intraperitoneal, intramuscular, and the like. When used in in vivo therapy, the antibodies of the invention are administered to a patient in effective amounts. As used herein, an "effective amount" is an amount sufficient to effect beneficial or desired clinical results (i.e., amounts that eliminate or reduce the patient's tumor burden). An effective amount can be administered in one or more administrations. For purposes of this invention, an effective amount of an antibody of the invention is an amount of the antibody that is sufficient to ameliorate, stabilize, prevent or delay the development of the Cripto- or activin B-associated disease state, particularly Cripto- or activin B-associated tumors.

An example of a typical treatment regime includes administering by intravenous infusion to the antibodies of the invention on a weekly schedule at a dose of about 2-5 mg/kg. The antibodies are administered in an outpatient chemoinfusion unit, unless the patient requires hospitalization. Other administration regimes known in the art are also included.

The abnormal condition can also be prevented or treated by administering an antibody of the invention to a group of cells having an aberration in a signal transduction pathway to an organism. The effect of administering a compound on organism function can then be monitored. The organism is preferably a human.

As used herein, "Cripto overexpression" means the expression of Cripto by a tissue or cell which expression is greater (e.g., by at least about 5%, 10%, 20%, 30%, 40%, 50%, or even by at least about 2, 3, 4, 5, or 10 fold) than the Cripto expression of normal tissue or cells in a statistically significant amount.

As used herein, "chemotherapeutic" means any agent identified in the art as having therapeutic effect on the inhibition of tumor growth, maintenance of inhibited tumor growth, and/or induction of remission, such as natural compounds, synthetic compounds, proteins, modified proteins, and radioactive compounds. Chemotherapeutic agents included herewith include agents that can be conjugated to the antibodies of the invention or alternatively agents that can be used in combination with the antibodies of the invention without being conjugated to the antibody. Exemplary chemotherapeutics that can be conjugated to the antibodies of the invention include, but are not limited to radioconjugates ($^{90}$Y, $^{131}$I, $^{99m}$Tc, $^{111}$In, $^{186}$Rh, etc.), tumor-activated prodrugs (maytansinoids, CC-1065 analogs, clicheamicin derivatives, anthracyclines, vinca alkaloids, etc.), ricin, diptheria toxin, and pseudomonas exotoxin.

Chemotherapeutic agents may be used in combination with the antibodies of the invention, rather than being conjugated thereto (i.e., nonconjugated chemotherapeutics), include, but are not limited to the following: platinums (i.e., cis platinum), anthracyclines, nucleoside analogs (purine and pyrimidine), taxanes, camptothecins, epipodophyllotoxins, DNA alkylating agents, folate antagonists, vinca alkaloids, ribonucleotide reductase inhibitors, estrogen inhibitors, progesterone inhibitors, androgen inhibitors, aromatase inhibitors, interferons, interleukins, monoclonal antibodies, taxol, camptosar, adriamycin (dox), 5-FU and gemcitabine. Such chemotherapeutics may be employed in the practice of the invention in combination with the antibodies of the invention by adjunctive administration of the antibody and the nonconjugated chemotherapeutic.

As used herein, "pharmaceutically acceptable carrier or excipient" means biologically inert compounds known in the art and employed in the administration of the antibodies of the invention. Acceptable carriers are well known in the art and are described, for example, in *Remington's Pharmaceutical Sciences*, Gennaro, ed., Mack Publishing Co., 1990. Acceptable carriers can include biocompatible, inert or bioabsorbable salts, buffering agents, oligosaccharides, or polysaccharides, polymers, viscoelastic compound such as hyaluronic acid, viscosity-improving agents, preservatives, and the like.

II. Antibodies of the Invention

The antibodies of the invention specifically bind to Cripto. As used herein, Cripto includes the CR-1 Cripto protein, the CR-3 Cripto protein, and fragments thereof. Such fragments may be entire domains, such as the extracellular or intracellular domains, the EGF-like domain, the cys-rich domain, the receptor binding domain, and the like. Such fragments may also include contiguous and noncontiguous epitopes in any domain of the Cripto protein. Examples of antigens used to raise antibodies specific for Cripto include, but are not limited to, CR40 (SEQ ID NO: 3), CR41 (SEQ ID NO: 4), CR43 (SEQ ID NO: 5), CR44 (SEQ ID NO: 6), CR49 (SEQ ID NO: 7), CR50 (SEQ ID NO: 8) and CR51 (SEQ ID NO: 9), the amino acid sequences of which are provided in Example 2.

The 188 amino acid sequence for CR-1 is as follows (SEQ ID NO: 1):

MDCRKMARFSYSVIWIMAISKVFELGLVAGLGHQEFARPSRGYLAFRDDS

IWPQEEPAIRPRSSQRVPPMGIQHSKELNRTCCLNGGTCMLGSFCACPPS

FYGRNCEHDVRKENCGSVPHDTWLPKKCSLCKCWHGQLRCFPQAFLPGCD

GLVMDEHLVASRTPELPPSARTTTFMLVGICLSIQSYY

The 188 amino acid sequence for CR-3 is as follows (SEQ ID NO: 2):

MDCRKMVRFSYSVIWIMAISKAFELGLVAGLGHQEFARPSRGDLAFRDDS

IWPQEEPAIRPRSSQRVLPMGIQHSKELNRTCCLNGGTCMLESFCACPPS

FYGRNCEHDVRKENCGSVPHDTWLPKKCSLCKCWHGQLRCFPQAFLPGCD

GLVMDEHLVASRTPELPPSARTTTFMLAGICLSIQSYY

In some embodiments, the antibodies of the invention bind to an epitope in the EGF-like domain of Cripto. The EGF-like domain spans from about amino acid residue 75 to about amino acid residue 112 of the mature Cripto protein. Epitopes in the EGF-like domain may comprise linear or nonlinear spans of amino acid residues. Examples of linear epitopes include, but are not limited to, about residues 75-85, 80-90, 85-95, 90-100, 95-105, 100-110, or 105-112. In some embodiments, the epitope in the EGF domain is an epitope formed in the conformationally native Cripto protein versus a denatured Cripto protein.

In other embodiments, the antibodies of the invention bind to an epitope in the cys-rich domain of Cripto. The cys-rich domain spans from about amino acid residue 114 to about amino acid residue 150 of the mature Cripto protein. Epitopes in the cys-rich domain may comprise linear or nonlinear spans of amino acid residues. Examples of linear epitopes include but are not limited to about residues 114-125, 120-130, 125-135, 130-140, 135-145, or 140-150. In certain embodiments, the epitope in the cys-rich domain is an epitope formed in the conformationally native Cripto protein versus a denatured Cripto protein Once antibodies are generated, binding of the antibodies to Cripto may be assayed using standard techniques known in the art, such as ELISA, while the presence of Cripto on a cell surface may be assayed using flow cytometry (FACS), as shown in Example 2. Any other techniques of measuring such binding may alternatively be used.

This invention provides antibodies (e.g., monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR sequences which specifically recognize a polypeptide of the invention) specific for Cripto or fragments thereof. The terms "specific" and "selective," when used to describe binding of the antibodies of the invention, indicate that the variable regions of the antibodies of the invention recognize and bind Cripto polypeptides. It will be understood that specific antibodies of the invention may also interact with other proteins (for example, S. aureus protein A or other antibodies in ELISA techniques) through interactions with sequences outside the variable regions of the antibodies, and, in particular, in the constant regions of the molecule.

Screening assays to determine binding specificity of an antibody of the invention (e.g., antibodies that specifically bind to an epitope the ligand/receptor binding domain or the domain spanning amino acid residues 46-62) are well known and routinely practiced in the art. For a comprehensive discussion of such assays, see Harlow et al. (Eds.), *Antibodies A Laboratory Manual*; Cold Spring Harbor Laboratory; Cold Spring Harbor, N.Y. (1988), Chapter 6. Antibodies that recognize and bind fragments of Cripto protein are also included, provided that the antibodies are specific for Cripto polypeptides. Antibodies of the invention can be produced using any method well known and routinely practiced in the art.

In some embodiments, the invention provides an antibody that specifically binds to an epitope in the ligand/receptor binding domain of Cripto. Antibody specificity is described in greater detail below. However, it should be emphasized that antibodies that can be generated from other polypeptides that have previously been described in the literature and that are capable of fortuitously cross-reacting with Cripto (e.g., due to the fortuitous existence of a similar epitope in both polypeptides) are considered "cross-reactive" antibodies. Such cross-reactive antibodies are not antibodies that are "specific" for Cripto. The determination of whether an antibody specifically binds to an epitope of Cripto is made using any of several assays, such as western blotting assays, that are well known in the art. For identifying cells that express Cripto and also for inhibiting Cripto ligand/receptor binding activity, antibodies that specifically bind to an extracellular epitope of the Cripto protein (i.e., portions of the Cripto protein found outside the cell) are particularly useful.

The invention also provides a cell-free composition comprising polyclonal antibodies, wherein at least one of the antibodies is an antibody of the invention. Antiserum isolated from an animal is an exemplary composition, as is a composition comprising an antibody fraction of an antiserum that has been resuspended in water or in another diluent, excipient, or carrier.

In other embodiments, the invention provides monoclonal antibodies. Monoclonal antibodies are highly specific, being directed against a single antigenic site. Further, in contrast to polyclonal preparations which typically include different antibodies directed against different epitopes, each monoclonal antibody is directed against a single determinant on the antigen. Monoclonal antibodies are useful to improve selectivity and specificity of diagnostic and analytical assay methods using antigen-antibody binding. Another advantage of monoclonal antibodies is that they can be synthesized by cultured cells such as hybridomas, uncontaminated by other immunoglobulins. Recombinant cells and hybridomas that produce such antibodies are also intended as aspects of the invention. See also discussions below.

In still other related embodiments, the invention provides an anti-idiotypic antibody specific for an antibody that is specific for Cripto. For a more detailed discussion of anti-idiotypic antibodies, see, e.g., U.S. Pat. Nos. 6,063,379 and 5,780,029.

It is well known that antibodies contain relatively small antigen binding domains that can be isolated chemically or by recombinant techniques. Such domains are useful Cripto binding molecules themselves, and also may be reintroduced into human antibodies, or fused to a chemotherapeutic or polypeptide. Thus, in still another embodiment, the invention provides a polypeptide comprising a fragment of a Cripto-specific antibody, wherein the fragment and associated molecule, if any, bind to the Cripto. By way of non-limiting example, the invention provides polypeptides that are single chain antibodies and CDR-grafted antibodies. For a more detailed discussion of CDR-grafted antibodies, see, e.g., U.S. Pat. No. 5,859,205 and discussion below.

In other embodiments, non-human antibodies may be humanized by any of the methods known in the art. Humanized antibodies are useful for in vivo therapeutic applications. In addition, recombinant "humanized" antibodies may be synthesized. Humanized antibodies are antibodies initially derived from a nonhuman mammal in which recombinant DNA technology has been used to substitute some or all of the amino acids not required for antigen binding with amino acids from corresponding regions of a human immunoglobulin light or heavy chain. That is, they are chimeras comprising mostly human immunoglobulin sequences in which the regions responsible for specific antigen-binding have been replaced.

Various forms of antibodies may be produced using standard recombinant DNA techniques (Winter and Milstein, 1991, *Nature* 349:293-99). For example, the monoclonal antibodies of this invention can be generated by well known hybridoma technology. For instance, animals (e.g., mice, rats or rabbits) can be immunized with purified or crude Cripto preparations, cells transfected with cDNA constructs encoding Cripto, cells that constitutively express Cripto, and the like. In addition, the antigen can be delivered as purified protein, protein expressed on cells, protein fragment or peptide thereof, or as naked DNA or viral vectors encoding the protein, protein fragment, or peptide. Sera of the immunized animals are then tested for the presence of anti-Cripto antibodies. B cells are isolated from animals that test positive, and hybridomas are made with these B cells.

Antibodies secreted by the hybridomas are screened for their ability to bind specifically to Cripto (e.g., binding to Cripto-transfected cells and not to untransfected parent cells) and for any other desired features, e.g., having the desired CDR consensus sequences, inhibiting (or not in the case of nonblockers) the binding between Cripto and ALK4 or between Cripto and Activin B.

Hybridoma cells that test positive in the screening assays are cultured in a nutrient medium under conditions that allow the cells to secrete the monoclonal antibodies into the culture medium. The conditioned hybridoma culture supernatant is then collected and antibodies contained in the supernatant are purified. Alternatively, the desired antibody may be produced by injecting the hybridoma cells into the peritoneal cavity of an unimmunized animal (e.g., a mouse). The hybridoma cells proliferate in the peritoneal cavity, secreting the antibody which accumulates as ascites fluid. The antibody may then be harvested by withdrawing the ascites fluid from the peritoneal cavity with a syringe.

The monoclonal antibodies can also be generated by isolating the antibody-coding cDNAs from the desired hybridomas, transfecting mammalian host cells (e.g., CHO or NSO cells) with the cDNAs, culturing the transfected host cells, and recovering the antibody from the culture medium.

The monoclonal antibodies of this invention can also be generated by engineering a cognate hybridoma (e.g., murine, rat or rabbit) antibody. For instance, a cognate antibody can be altered by recombinant DNA technology such that part or all of the hinge and/or constant regions of the heavy and/or light chains are replaced with the corresponding components of an antibody from another species (e.g., human). Generally, the variable domains of the engineered antibody remain identical or substantially so to the variable domains of the cognate antibody. Such an engineered antibody is called a chimeric antibody and is less antigenic than the cognate antibody when administered to an individual of the species from which the hinge and/or constant region is derived (e.g., a human). Methods of making chimeric antibodies are well known in the art. Human constant regions include those derived from IgG1 and IgG4.

The monoclonal antibodies of this invention also include fully human antibodies. They may be prepared using in vitro-primed human splenocytes, as described by Boerner et al., 1991, *J. Immunol.* 147:86-95, or using phage-displayed antibody libraries, as described in, e.g., U.S. Pat. No. 6,300,064.

Alternatively, fully human antibodies may be prepared by repertoire cloning as described by Persson et al., 1991, *Proc. Natl. Acad. Sci. USA* 88:2432-36; and Huang and Stollar, 1991, *J. Immunol. Methods* 141:227-36. In addition, U.S. Pat. No. 5,798,230 describes preparation of human monoclonal antibodies from human B cells, wherein human antibody-producing B cells are immortalized by infection with an Epstein-Barr virus, or a derivative thereof, that expresses Epstein-Barr virus nuclear antigen 2 (EBNA2), a protein required for immortalization. The EBNA2 function is subsequently shut off, resulting in an increase in antibody production.

Some other methods for producing fully human antibodies involve the use of non-human animals that have inactivated endogenous Ig loci and are transgenic for un-rearranged human antibody heavy chain and light chain genes. Such transgenic animals can be immunized with Cripto and hybridomas made from B cells derived therefrom. These methods are described in, e.g., the various GenPharm/Medarex (Palo Alto, Calif.) publications/patents concerning transgenic mice containing human Ig miniloci (e.g., U.S. Pat. No. 5,789,650); the various Abgenix (Fremont, Calif.) publications/patents with respect to XENOMICE™ (e.g., U.S. Pat. Nos. 6,075, 181, 6,150,584 and 6,162,963; Green et al., 1994, *Nature Genetics* 7:13-21; and Mendez et al., 1997, *Nature Genetics* 15:146-56); and the various Kirin (Japan) publications/patents concerning "transomic" mice (e.g., EP 843 961, and Tomizuka et al., 1997, *Nature Genetics* 16:1433-43). See also, e.g., U.S. Pat. No. 5,569,825, WO00076310, WO00058499 and WO00037504, incorporated by reference herein in their entireties.

The monoclonal antibodies of this invention also include humanized versions of cognate anti-Cripto antibodies derived from other species. A humanized antibody is an antibody produced by recombinant DNA technology, in which some or all of the amino acids of a human immunoglobulin light or heavy chain that are not required for antigen binding (e.g., the constant regions and the framework regions of the variable domains) are used to substitute for the corresponding amino acids from the light or heavy chain of the cognate, nonhuman antibody. By way of example, a humanized version of a murine antibody to a given antigen has on both of its heavy and light chains (1) constant regions of a human antibody; (2) framework regions from the variable domains of a human antibody; and (3) CDRs from the murine antibody. When necessary, one or more residues in the human framework regions can be changed to residues at the corresponding positions in the murine antibody so as to preserve the binding affinity of the humanized antibody to the antigen. This change is sometimes called "back mutation." Humanized antibodies generally are less likely to elicit an immune response in humans as compared to chimeric human antibodies because the former contain considerably fewer non-human components.

The methods for making humanized antibodies are described in, e.g., Winter EP 239 400; Jones et al., 1986, *Nature* 321:522-25; Riechmann et al., 1988, *Nature* 332:323-27 (1988); Verhoeyen et al., 1988, *Science* 239:1534-36; Queen et al., 1989, *Proc. Natl. Acad. Sci. USA* 86:10029-33; U.S. Pat. No. 6,180,370; and Orlandi et al., 1989, *Proc. Natl. Acad. Sci. USA* 86:3833-37. See also, e.g., PCT patent application No. 94/04679. Primatized antibodies can be produced similarly using primate (e.g., rhesus, baboon and chimpanzee) antibody genes. Further changes can then be introduced into the antibody framework to modulate affinity or immunogenicity. See, e.g., U.S. Pat. Nos. 5,585,089, 5,693,761, 5,693,762, and 6,180,370.

Generally, the transplantation of murine (or other non-human) CDRs onto a human antibody is achieved as follows. The cDNAs encoding heavy and light chain variable domains are isolated from a hybridoma. The DNA sequences of the variable domains, including the CDRs, are determined by sequencing. The DNAs encoding the CDRs are transferred to the corresponding regions of a human antibody heavy or light chain variable domain coding sequence by site directed mutagenesis. Then human constant region gene segments of a desired isotype (e.g, γ1 for CH and κ for CL) are added. The humanized heavy and light chain genes are co-expressed in mammalian host cells (e.g., CHO or NSO cells) to produce soluble humanized antibody. To facilitate large scale production of antibodies, it is often desirable to produce such humanized antibodies in bioreactors containing the antibody-expressing cells, or to produce transgenic mammals (e.g., goats, cows, or sheep) that express the antibody in milk (see, e.g., U.S. Pat. No. 5,827,690).

At times, direct transfer of CDRs to a human framework leads to a loss of antigen-binding affinity of the resultant antibody. This is because in some cognate antibodies, certain amino acids within the framework regions interact with the CDRs and thus influence the overall antigen binding affinity of the antibody. In such cases, "back mutations" (supra) should be introduced into the framework regions of the acceptor antibody in order to retain the antigen-binding activity of the cognate antibody.

The general approach of making back mutations is known in the art. For instance Queen, et al., 1989, *Proc. Natl. Acad. Sci. USA* 86:10029-33, Co et al., 1991, *Proc. Natl. Acad. Sci. USA* 88:2869-73, and WO 90/07861 (Protein Design Labs Inc.) describe an approach that involves two key steps. First, the human V framework regions are chosen by computer analysis for optimal protein sequence homology to the V region framework of the cognate murine antibody. Then, the tertiary structure of the murine V region is modeled by computer in order to visualize framework amino acid residues that are likely to interact with the murine CDRs, and these murine amino acid residues are then superimposed on the homologous human framework.

Under this two-step approach, there are several criteria for designing humanized antibodies. The first criterion is to use as the human acceptor the framework from a particular human immunoglobulin that is usually homologous to the non-human donor immunoglobulin, or to use a consensus framework from many human antibodies. The second criterion is to use the donor amino acid rather than the acceptor if the human acceptor residue is unusual and the donor residue is typical for human sequences at a specific residue of the framework. The third criterion is to use the donor framework amino acid residue rather than the acceptor at positions immediately adjacent to the CDRs.

One may also use a different approach as described in, e.g., Tempest, 1991, *Biotechnology* 9: 266-71. Under this approach, the V region frameworks derived from NEWM and REI heavy and light chains, respectively, are used for CDR-grafting without radical introduction of mouse residues. An advantage of using this approach is that the three-dimensional structures of NEWM and REI variable regions are known from X-ray crystallography and thus specific interactions between CDRs and V region framework residues can be readily modeled.

The humanized antibody of this invention may contain a mutation (e.g., deletion, substitution or addition) at one or more (e.g., 2, 3, 4, 5, 6, 7 or 8) of certain positions in the heavy chain such that an effector function of the antibody (e.g., the ability of the antibody to bind to a Fc receptor or a complement factor) is altered without affecting the antibody's ability to bind to Cripto (U.S. Pat. No. 5,648,260). These heavy chain positions include, without limitation, residues 234, 235, 236, 237, 297, 318, 320 and 322 (EU numbering system). The humanized antibody can, for instance, contain the mutations L234A (i.e., replacing leucine at position 234 of an unmodified antibody with alanine) and L235A (EU numbering system) in its heavy chain.

In addition, the humanized antibody of this invention may contain a mutation (e.g., deletion or substitution) at an amino acid residue that is a site for glycosylation, such that the glycosylation site is eliminated. Such an antibody may be clinically beneficial for having reduced effector functions or other undesired functions while retaining its Cripto binding affinity. Mutations of glycosylation sites can also be beneficial for process development (e.g., protein expression and purification). For instance, the heavy chain of the antibody may contain the mutation N297Q (EU numbering system) such that the heavy chain can no longer be glycosylated at this site.

In still other embodiments, the heavy and/or light chains of the antibody of this invention contain mutations that increase affinity for binding to Cripto and thereby increase potency for treating Cripto-mediated disorders.

The monoclonal antibodies of this invention may further include other moieties to effect or enhance a desired function. For instance, the antibodies may include a toxin moiety (e.g., tetanus toxoid or ricin) or a radionuclide (e.g., $^{111}$In or $^{90}$Y) for killing of cells targeted by the antibodies (see, e.g., U.S. Pat. No. 6,307,026). The antibodies may include a moiety (e.g., biotin, fluorescent moieties, radioactive moieties, histidine tag or other peptide tags) for easy isolation or detection. The antibodies may also include a moiety that can prolong their serum half life, for example, a polyethylene glycol (PEG) moiety, and a member of the immunoglobulin super family or fragment thereof (e.g., a portion of human IgG1 heavy chain constant region such as the hinge, CH2 and CH3 regions).

Antibody fragments and univalent antibodies may also be used in the methods and compositions of this invention. Univalent antibodies comprise a heavy chain/light chain dimer bound to the Fc (or stem) region of a second heavy chain. "Fab region" refers to those portions of the chains which are roughly equivalent, or analogous, to the sequences which comprise the Y branch portions of the heavy chain and to the light chain in its entirety, and which collectively (in aggregates) have been shown to exhibit antibody activity. A Fab protein includes aggregates of one heavy and one light chain (commonly known as Fab') as well as tetramers which correspond to the two branch segments of the antibody Y (commonly known as F(ab)2) whether any of the above are covalently or non-covalently aggregated, so long as the aggregation is capable of specifically reacting with a particular antigen or antigen family.

III. Signal Modulation

The antibodies of the invention can inhibit Cripto activity and/or Cripto interactions with its ligands. Overexpression of Cripto activity can lead to a de-differentiated state promoting mesenchymal cell characteristics, increased proliferation, and cell migration (Salomon et al., 1999, *BioEssays* 21:61-70; Ciardiello et al., 1994, *Oncogene* 9:291-98; and Baldassarre et al., 1996, *Int. J. Cancer* 66:538-43), phenotypes associated with cell transformation seen in neoplasia.

One method of testing the activity of anti-Cripto antibodies and their ability to inhibit Cripto activity is with an F9-Cripto knock-out (KO) cell line (Minchiotti at al., 2000, *Mech. Dev.* 90:133-42). Cripto stimulates Smad2 phosphorylation and the transcription factor FAST in *Xenopus* embryos, and the activity of the transcription factor FAST can be monitored by measuring the luciferase activity from a FAST regulatory element-luciferase reporter gene (Saijoh et al., 2000, *Mol. Cell* 5:35-47). F9-Cripto KO cells have null mutations in the Cripto gene and cannot transduce Cripto-dependent signaling (Minchiotti et al., supra). Cripto activity can be assessed in the F9 Cripto KO cells by transfecting them with Cripto, FAST, and the FAST regulatory element-luciferase gene constructs. No Cripto-dependent FAST luciferase activity will be seen in these cell lines unless Cripto cDNA and FAST cDNA are transfected into them. Antibodies capable of blocking Cripto-dependent Nodal signaling are antibodies that block Cripto activity.

Other assays capable of measuring the activity of Cripto can be employed by those of skill in the art, such as a growth in soft agar assay (see Example 4 below). The ability of cells to grow in soft agar is associated with cell transformation and the assay is a classical in vitro assay for measuring inhibition of tumor cell growth. Other assays useful in determining inhibition of activity include in vitro assays on plastic, and the like.

In certain embodiments, the antibodies of the invention bind to Cripto and inhibit Cripto-Activin B interactions. We have discovered that Cripto can bind to Activin B and inhibit the Activin B signaling pathway. Activin B can inhibit proliferation of tumor cells (Risbridger et al., 2001, *Endocr. Rev.* 22:836-58). Cripto binding to Activin B also can disrupt Activin B-induced inhibition of proliferation.

One method for testing the activity of anti-Cripto antibodies and their ability to inhibit Cripto-Activin B interactions is by measuring the ability of the antibody to prevent Cripto-mediated disruption of Activin B-induced inhibition of proliferation. One such method is described in Example 9. A method for directly testing the ability of anti-Cripto antibodies to inhibit Cripto-Activin B interactions is described in Example 11.

IV. Therapeutic Uses

Antibodies of the invention are also useful for therapeutic purposes, such as inhibition of tumor cell growth, diagnostic purposes to detect or quantitate Cripto, and purification of Cripto.

In some embodiments of the invention, antibodies are provided which are capable of binding specifically to Cripto and which inhibit growth of tumor cells in a patient, especially where the tumor growth is mediated by the loss or decrease of Activin B signaling. In certain embodiments, the tumor cells are brain, head, neck, prostate, breast, testicular, colon, lung, ovary, bladder, uterine, cervical, pancreatic and stomach tumor cells.

In other embodiments, antibodies are provided which are capable of binding specifically to Cripto and which inhibit growth of tumor cells which overexpress Cripto. In one embodiment, the tumor cells are cell lines which overexpress Cripto, such as cell lines derived from brain, breast, testicular, colon, lung, ovary, bladder, uterine, cervical, pancreatic and stomach cancer.

Anti-Cripto antibodies may be screened for in vivo activity as potential anticancer agents following standard protocols used by those of skill in the art, as illustrated in Example 4 below. Example of such protocols are outlined by the National Cancer Institute (NCI) in their "in vivo cancer models screening" protocols, NIH publication number 84-2635 (February 1984).

In other embodiments of the invention, the antibodies of the invention are used to treat a patient having a cancerous tumor.

The antibodies of the invention can be combined with a pharmaceutically acceptable excipient and administered in a therapeutically effective dose to a patient. For a discussion of methods of inhibiting growth of tumors, see, e.g., U.S. Pat. No. 6,165,464.

Also included are methods of treating a mammal suffering from a disorder associated with elevated levels of Cripto or decreased levels of Activin B wherein the method comprises administering to the mammal an effective amount of an antibody that specifically binds to an epitope in the ligand/receptor binding domain of Cripto, including but not limited to where the epitope is in an EGF-like domain or a cys-rich domain of Cripto.

Also included are methods of treating a mammal suffering from a disorder associated with elevated levels of Cripto wherein the method comprises administering to the mammal an effective amount of an antibody which specifically forms a complex with Cripto and is directed to the epitope to which an antibody selected from the group consisting of A6C12.11, A6F8.6 (ATCC ACCESSION NO. PTA-3318), A7H1.19, A8F1.30, A8G3.5 (ATCC ACCESSION NO. PTA-3317), A8H3.1 (ATCC ACCESSION NO. PTA-3315), A8H3.2, A10A10.30, A19A10.30, A10B2.17, A10B2.18 (ATCC ACCESSION NO. PTA-3311), A27F6.1 (ATCC ACCESSION NO. PTA-3310), A40G12.8 (ATCC ACCESSION NO. PTA-3316), A2D3.23, A7A10.29, A9G9.9, A15C12.10, A15E4.14, A17A2.16, A17C12.28, A17G12.1 (ATCC ACCESSION NO. PTA-3314), A17H6.1, A18B3.11 (ATCC ACCESSION NO. PTA-3312), A19E2.7, B3F6.17 (ATCC ACCESSION NO. PTA-3319), B6G7.10 (ATCC ACCESSION NO. PTA-3313), 1-1A4C.2, 2-2C9.2, 2-3H9.2, 2-4E5.6, 2-4D1.3, 3-4E8.3, 3-3G1.1, 4-2F6, 4-3A7 and 4-1E2 is directed.

Diagnosis via detection of Cripto is readily accomplished through standard binding assays using the novel antibodies of the invention, allowing those of skill in the art to detect the presence of Cripto specifically in a wide variety of samples, cultures, and the like.

The hybridoma cells A27F6.1, A10B2.18, A18B3.11, B6G7.10, A17G12.1, A8H3.1, A40G12.8, A8G3.5, A6F8.6, B3F6.17, 1-1A4-C2, 2-2C9.2, 2-4E5.6, 3-4E8.3, and 3-3G1.1 were deposited with the American Type Culture Collection at 12301 Parklawn Drive, Rockville, Md. 20852 under the terms of the Budapest Treaty as ATCC Accession No. PTA-3310 (A27F6.1), ATCC Accession No. PTA-3311 (A10B2.18), ATCC Accession No. PTA-3312 (A18B3.11), ATCC Accession No. PTA-3313 (B6G7.10), ATCC Accession No. PTA-3314 (A17G12.1), ATCC Accession No. PTA-3315 (A8H3.1), ATCC Accession No. PTA-3316 (A40G12.8), ATCC Accession No. PTA-3317 (A8G3.5), ATCC Accession No. PTA-3318 (A6F8.6), ATCC Accession No. PTA-3319 (B3F6.17), ATCC Accession No. PTA-4697 (1-1A4-C2), PTA-4698 (2-2C9.2), PTA-4699 (2-4E5.6), PTA-4700 (3-4E8.3), and PTA-4701 (3-3G1.1).

Kits comprising an antibody of the invention for any of the purposes described herein are also comprehended. In general, a kit of the invention also includes a control antigen for which the antibody is immunospecific. Embodiments include kits comprising all reagents and instructions for the use thereof.

V. Examples

Additional features of the invention will be apparent from the following Examples. It should be understood that the following Examples are for purposes of illustration only, and are not to be construed as limiting the scope of the invention in any manner.

Example 1

Expression and Purification of Cripto

An expression plasmid designated pSGS480 was constructed by sub-cloning a cDNA encoding amino acid residues 1 to 169 of a human Cripto protein (amino acids 1-169 of SEQ ID NO: 1), fused to human IgG$_1$ Fc domain (i.e., "CR (del C)-Fc") into vector pEAG1100. For a more detailed description of this vector, see U.S. Patent Application Ser. No. 60/233,148, filed Sep. 18, 2000. The vector pEAG1100 is a derivative of GIBCO-BRL Life Technologies plasmid pCMV-Sport-betagal, the use of which in CHO transient transfections was described by Schifferli et al., 1999, *Focus* 21:16. It was made by removing the reporter gene beta-galactosidase NotI fragment from the plasmid pCMV-Sport-Betagal (catalog number 10586-014) as follows: the plasmid was digested with NotI and EcoRV, the 4.38 kb NotI vector backbone fragment was gel-purified and ligated. Ligated DNA was transformed into competent *E. coli* DH5α. pEAG1100 was isolated as a plasmid containing the desired recombinant from an isolated single colony. The sequence of pEAG1100 spanning the promoter, polylinker, and transcription termination signal was confirmed.

Plasmid pSGS480 was transiently transfected into CHO cells and the cells were grown at 28° C. for 7 days. The presence of CR(del C)-Fc protein in these cells and the conditioned media was examined by western blot analysis. For western blot analysis, conditioned media and cells from Cripto transfected cells were subjected to SDS-PAGE on 4-20% gradient gels under reducing conditions, transferred electrophoretically to nitrocellulose, and the Cripto fusion protein was detected with a rabbit polyclonal antiserum raised against a Cripto 17-mer peptide (comprising residues 97-113 of SEQ ID NO: 1)-keyhole limpet hemocyanin (KLH) conjugate. After centrifugation to remove the cells, western blot analysis showed that the CR(del C)-Fc protein was efficiently secreted into the conditioned media (supernatant). The supernatant was applied to Protein A-Sepharose® (Pharmacia), and bound protein was eluted with 25 mM sodium phosphate pH 2.8, 100 mM NaCl. The eluted protein was neutralized with 0.5 M sodium phosphate at pH 8.6, and analyzed for total protein content from absorbance measurements at 240-340 nm, and for purity by SDS-PAGE. The eluted protein was filtered through a 0.2 micron filter, and stored at −70° C.

Example 2

Generation and Screening of Antibodies

The eluted CR(del C)-Fc protein, as well as other Cripto polypeptides, are injected into mice, and standard techniques known to those of skill in the art are used to generate hybridomas and monoclonal antibodies.

A. Generation of Antibodies

Female Robertsonian mice (Jackson Labs) were immunized intraperitoneally with 25 µg of purified human CR(del C)-Fc emulsified with complete Freund's adjuvant ("FCA"; GibcoBRL #15721-012). They were boosted two times intraperitoneally (IP) with 25 µg of CR(del C)-Fc emulsified with incomplete Freund's adjuvant ("FIA"; GibcoBRL #15720-014) and once on Protein A beads. The sera were screened and 3 weeks after the last boost, the mouse with the best titer was boosted intraperitoneally with 50 µg soluble CR(del C)-Fc three days before fusion. The mouse was boosted intravenously (IV) with 50 µg CR(del C)-Fc the day before fusion.

Mouse spleen cells were fused with FL653 myeloma cell at a 1 spleen: 6 myeloma ratio and were plated at 100,000, 33,000 and 11,000 cells per well into 96 well tissue culture plates in selection media. Wells positive for growth were screened by FACS and ELISA a week later. Two fusions were performed.

B. Screening of Antibodies

Supernatants resulting from the first or second fusion were screened first on ELISA plates for recognition of Cripto(del C) and/or Cripto EGF-like domain proteins. A control fusion protein (LT-beta receptor-Fc) was coated on ELISA plates to discard monoclonal antibodies that recognized the human Fc epitope. The ELISA was performed as described below in section C. In the first fusion, primary supernatants were also screened by FACS for their ability to recognize cell surface Cripto protein on the testicular tumor cell line NCCIT. In the case of the second fusion, the ability of supernatants to recognize Cripto on two tumor cell lines, NCCIT and the breast cancer line, DU4475, was analyzed by FACS. Secondary screens included testing the monoclonal antibody supernatant's ability to recognize cell surface Cripto on a panel of tumor cell lines (see Tables 1 and 2 for results), ability of monoclonal antibodies to recognize human Cripto immunohistochemically on human breast and colon tumor tissue sections, ability of monoclonal antibodies to block signalling in a Cripto-Nodal signalling assay, ability to block growth of tumor cell lines on plastic or in soft agar assays, and ability to internalize cell surface Cripto.

C. ELISA

The ELISA assays were performed as follows:

Materials:
  Plates: Costar high-binding Easy-wash 96W plates (07-200-642)
  Secondary antibody: Pierce Gt anti-Ms IgG (H+L)-HRP (P131430)
  Substrate: Pierce TMB Substrate Kit (34021)
  Stop solution: 1N $H_2SO_4$ Buffers:
  Binding buffer: 0.1 M $NaHPO_4$ pH 9.0
  Blocking buffer: PBS+10% Donor Calf Serum
  Wash buffer: PBS+0.1% Tween 20
  Antigens CR(del C)-Fc and CR-EGF-Fc, control hu IgG1 fusion protein were diluted in binding buffer to 500 ng/ml. 100 µl were added per well and incubated for 1 hr at 37° C. or overnight at 4° C. The liquid was decanted and the plate inverted and blotted until dry. 250 µl/well blocking buffer was then added, followed by incubation for 30 min. at 37° C. Again, the liquid was decanted and the plate inverted and blotted until dry. Supernatants were diluted 1:50 in wash buffer, and plated at 50 µl/well, followed by incubation for 1 hour at room temperature. Plates were washed 3× vigorously with 250 µl/well wash buffer. Then 100 µl/well secondary antibody diluted in wash buffer at 1:10,000 was added, followed by incubation for 30 min. at room temperature. Plates were then washed 3× vigorously with 250 µl/well wash buffer, then substrate added at 100 µl/well. Color was permitted to develop until sufficiently dark, then 100 µl/well stop solution was added and the plates read for absorbance at 450 nm.

In certain experiments, we coated 96 well plates with Cripto proteins by adding 100 µl of 0.5 µg/ml Cripto proteins in 0.1 M $NaHPO_4$ (pH 9.0) and incubating at 37° C. for 1 hr. We blocked the plates with PBS/10% DCS. We added antibodies diluted in PBS/0.05% Tween® 20 at 50 µl/well and incubated at 37° C. for 1 hr. We washed with PBS/0.05% Tween® 20 and probed with anti-mouse-HRP (Pierce). We detected bound antibodies by adding TMB, stopped the reaction with 1N $H_2SO_4$ and read at 450 nm.

In still other experiments, we coated 96 well plates by adding to each well 100 µl of 3-5 µg/ml Activin B or another ligand in 50 mM carbonate (pH 9.5). We incubated the plates for 1 hr. at room temperature and blocked overnight with TBS/1% BSA overnight at 4° C. We incubated the plate with CR-Fc or ALK4-Fc in blocking buffer at room temperature, washed in TBST and probed with anti-human-AP (Jackson). We washed the plate in TBST, once in 10× substrate buffer (200 mM Tris-HCl, 10 mM $MgCl_2$, pH 9.8) and added CSPD and Sapphire (Applied Biosystems).

D. Flow Cytometry

Cripto positive cell lines may be used to assay the monoclonal antibodies for binding to Cripto using cell surface staining and flow cytometry as follows:

Release cells from T162 flasks with 2 ml PBS with 5 mM EDTA, 10 min., 37° C. Bring up to 20 ml with media with serum, pipetting up and down several times to unclump cells. Spin at 1200 rpm for 5 minutes. Wash cells with 5-10 ml 4° C. PBS with 0.1% BSA (wash buffer). Spin at 1200 rpm for 5 minutes. Resuspend at $4 \times 10^6$-$10^7$/ml in wash buffer. Keep on ice.

Prepare antibodies for staining. Purified antibodies are diluted to 1-10 µg/ml in wash buffer. Add 50 µl of cells to a 96-well Linbro V bottomed plate (ICN 7632105). Plate one well of cells for each control for each cell line to be analyzed, including cells for no antibody, secondary antibody only, hybridoma media, positive control antibody supernatant, if available, or purified, and an IgG subclass control (if using purified antibodies).

Plate one well of cells for each experimental sample for each cell line to be analyzed. Spin plate, 1200 rpm for 5 minutes, using a table top centrifuge at 4° C. Flick out buffer by inverting the plate and shaking until the liquid is substantially discarded. Add 40-50 µl of antibodies (or wash buffer for the no-antibody and secondary antibody-only control wells) to wells. Incubate at least 30 min.-1 hour at 4° C. Spin plate, 1200 rpm for 5 minutes. Flick out antibody solutions. Wash wells twice with 200 µl wash buffer per well, spinning after each wash. Flick out buffer.

Resuspend cells in each well in 50 µl of 1:200 dilution (in wash buffer) of R-PE tagged goat anti-mouse IgG, Fc Specific (Jackson Immunoresearch Laboratories Cat# 115-116-071). Incubate 20 min, 4° C., in the dark. Add 150 µl wash buffer to cells in each well. Spin plate at 1200 rpm for 5 minutes. Wash once with 200 µl wash buffer per well. Resuspend cells in 150 µl 1% PFA in PBS. Transfer contents of each well to separate tubes (5 ml Falcon polystyrene round bottomed tube-352052). Wrap tubes in tin foil.

The contents of the tubes are then read by flow cytometry.

The results of two screenings of certain monoclonal antibodies analyzed by this method yielded the following results, summarized in Tables 1 and 2 below, wherein the first column provides the designated names for the hybridoma subclones, the next two columns show the results of ELISA screens, and the remaining columns show flow cytometry analysis results on four cripto-positive cell lines. The results are given in units of mean fluorescent index (MFI).

TABLE 1

Anti-Cripto Monoclonal Antibody Characterization

| Hybridoma Subclone | ATCC deposit no. | ELISA Cripto delC Sups | ELISA Cripto EGFlike domain Sups | DU4475 MFI | NCCIT MFI | GEO MFI | HT3 MFI |
|---|---|---|---|---|---|---|---|
| Control-ELISA | | 0.06 | 0.07 | | | | |
| Control-MouseIg | | | | 14 | 9 | 37 | 18 |
| A6C12.11 | | 2.21 | 0.07 | 11 | 35 | 29 | 8 |
| A6F8.6 | PTA-3318 | 2.32 | 0.08 | 11 | 50 | 29 | 10 |
| A7H1.19 | | 2.14 | 0.09 | 14 | 34 | 27 | 12 |
| A8F1.30 | | 2.15 | 0.1 | 17 | 27 | 32 | 28 |
| A8G3.5 | PTA-3317 | 2.39 | 0.09 | 9 | 30 | 25 | 15 |
| A8H3.1 | PTA-3315 | 2.4 | 1.7 | 9 | 44 | 23 | 10 |
| A8H3.2 | | 2.54 | 0.07 | 13 | 13 | 16 | 14 |
| A19A10.30 | | 2.02 | 0.09 | 9 | 40 | 20 | 10 |
| A10B2.18 | PTA-3311 | 2.36 | 0.07 | 40 | 63 | 100 | 43 |
| A27F6.1 | PTA-3310 | 2.28 | 1.19 | 9 | 44 | 26 | 17 |
| A40G12.8 | PTA-3316 | 2.27 | 1.59 | 10 | 47 | 26 | 16 |

TABLE 2

Anti-Cripto Monoclonal Antibody Characterization

| Hybridoma Subclone | ATCC deposit no. | ELISA Cripto delC | ELISA Cripto EGFlike domain | DU4475 MFI | NCCIT MFI | GEO MFI | HT3 MFI |
|---|---|---|---|---|---|---|---|
| Control-ELISA | | 0.05 | 0.05 | | | | |
| Control-MouseIg | | | | 10 | 6 | 4 | 6 |
| A2D3.23 | | 0.93 | 0.90 | 73 | 138 | 37 | 27 |
| A7A10.29 | | 1.37 | 0.07 | 75 | 83 | 33 | 83 |
| A9G9.9 | | 1.39 | 0.07 | 52 | 62 | 32 | 82 |
| A15C12.10 | | 1.42 | 0.06 | 46 | 55 | 25 | 93 |
| A15E4.14 | | 1.38 | 0.06 | 50 | 63 | 23 | 95 |
| A17A2.16 | | 1.40 | 0.06 | 76 | 97 | 41 | 81 |
| A17C12.28 | | 0.96 | 0.97 | 6 | 16 | 3 | 22 |
| A17G12.1 | PTA-3314 | 1.30 | 1.37 | 61 | 66 | 28 | 78 |
| A17H6.1 | | 1.38 | 0.05 | 35 | 30 | 5 | 28 |
| A18B3.11 | PTA-3312 | 1.36 | 1.38 | 50 | 42 | 33 | 65 |
| A19E2.7 | | 1.40 | 0.06 | 53 | 59 | 26 | 99 |
| B3F6.17 | PTA-3319 | 1.37 | 0.06 | 77 | 51 | 39 | 89 |
| B6G7.10 | PTA-3313 | 1.38 | 1.40 | 28 | 22 | 22 | 56 |
| B11H8.4 | | 1.41 | 0.06 | 59 | 101 | 39 | 107 |
| B12C12.5 | | 1.10 | 1.04 | 27 | 14 | 23 | 59 |
| B15A2.6 | | 1.40 | 0.06 | 36 | 44 | 22 | 59 |
| C4A2.16 | | 1.40 | 0.06 | 24 | 36 | 22 | 65 |

We also employed numerous other immunization protocols using the CR(del C)-Fc protein as well as region-specific Cripto peptides as described below. In these cases, we also generated hybridomas as described. The Cripto peptides were used in addition to or in place of the CR(del C)-Fc protein. These protocols identified some of the antibodies of the invention. As will be appreciated by one of skill in the art, these experiments indicate that multiple, diverse immunization protocols may be used to generate the antibodies of the invention.

In one exemplary immunization protocol, eight-week-old female RBF mice (Jackson Labs, Bar Harbor, Me.) were immunized intraperitoneally (IP) with an emulsion containing either 50 μg soluble CR(del C)-Fc recombinant protein or a region-specific Cripto peptide conjugated to keyhole limpet hemocyanin (KLH) and Freund's complete adjuvant (FCA, Sigma Chemical Co., St. Louis, Mo.). Specifically, CR(del C)-Fc protein or Cripto peptide CR40 (aa36-42; SEQ ID NO: 3)-KLH was diluted into phosphate buffered saline, pH 7.2 at an estimated concentration of 2 mg/ml. To this protein, an equal volume of FCA was added prior to emulsification and immunization. Fifty μl containing 50 μg of emulsified CR(del C)-Fc or Cripto peptide CR40-KLH was IP administered into each mouse for the primary immunization. All subsequent immunizations were similarly dosed using either Freund's Incomplete Adjuvant (FIA) or RIBI adjuvant$_{1,2}$ (Sigma Chemical Co., St. Louis, Mo.), as described below. Booster immunizations were administered every two to three weeks. Serum samples from immunized mice were collected before the first immunization, 7 days after the booster immunizations, and again prior to lymphocyte cell fusions. Serum titers were measured using both an ELISA and flow cytometry assay described below.

Various exemplary immunization protocols with different Cripto antigens, as well as antibodies identified thereby, are as follows:

ANTIGEN 1—(CR(del C)-Fc):

| Protocol A: | |
|---|---|
| 1° | 50 μg CR(del C)-Fc (IP) + FCA |
| 2° | 50 μg CR(del C)-Fc (IP) + FIA |
| 3° | 50 μg CR(del C)-Fc (IP) + FIA |
| 4° | 25 μg CR(del C)-Fc (IV) in PBS |

TABLE 3

Anti-Cripto Monoclonal Antibody Characterization

| Purified mAbs | ELISA Cripto delC | ELISA Cripto CFC domain | LS174T MFI | NCCIT MFI | GEO MFI | H727 MFI | HT3 MFI |
|---|---|---|---|---|---|---|---|
| 1-1A4C.2 | 0.197 | 0.682 | 141 | 371 | 441 | 503 | 596 |
| 2-2C9.2 | 0.567 | 0.796 | 305 | 407 | 309 | 820 | 205 |
| 2-3H9.2 | 0.637 | 0.354 | 127 | 84 | 123 | 191 | 59 |
| 2-4E5.6 | 0.626 | 0.328 | 90 | 71 | 127 | 183 | 47 |
| 2-4D1.3 | 0.866 | 0.946 | 31 | 18 | 67 | 197 | 104 |
| Control IgG | 0.05 | 0.05 | 33 | 16 | 47 | 74 | 19 |

| Protocol B: | |
|---|---|
| 1° | 50 μg CR(del C)-Fc (IP) + FCA |
| 2° | 50 μg CR(del C)-Fc (IP) + FIA |
| 3° | 50 μg CR(del C)-Fc (IP) + FIA |
| 4° | 50 μg CR(del C)-Fc (IP) + FIA |
| 5° | 25 μg CR(del C)-Fc (IV) in PBS |

ANTIGEN 2—(CR(del C)-Fc+CR40 peptide):

| Protocol C: | |
|---|---|
| 1° | 50 μg CR(del C)-Fc (IP) + FCA |
| 2° | 50 μg CR(del C)-Fc (IP) + FIA |
| 3° | 50 μg CR(del C)-Fc (IP) + FIA |
| 4° | 50 μg A10B2-KLH (IP) + FIA |
| 5° | 50 μg A10B2-KLH (IP) + FIA |

TABLE 4

Anti-Cripto Monoclonal Antibody Characterization

| Hybridoma Subclone | ELISA Cripto delC | ELISA Cripto CFC domain | LS174T MFI | NCCIT MFI | GEO MFI | H727 MFI | HT3 MFI |
|---|---|---|---|---|---|---|---|
| 3-4E8.3 | 0.6 | 0.3 | ND | ND | ND | ND | ND |
| 3-3G1.1 | 0.5139 | 0.9206 | 298 | 97 | 1099 | 677 | 1538 |
| Control IgG | 0.05 | 0.05 | 33 | 17 | 88 | 19 | 10 |

ND = not determined

ANTIGEN 3—(CR(del C)-Fc+LS174 T tumor membrane preparation):

| Protocol D: | |
|---|---|
| 1° | 50 μg CR(del C)-Fc (IP) + FCA |
| 2° | 50 μg CR(del C)-Fc (IP) + FIA |
| 3° | 50 μg CR(del C)-Fc (IP) + FIA |
| 4° | ~50 μg LS174T Cripto (IP) + RIBI |

TABLE 5

Anti-Cripto Monoclonal Antibody Characterization

| Hybridoma Subclone | ELISA Cripto delC | ELISA Cripto CFC domain | H727 MFI | HT3 MFI |
|---|---|---|---|---|
| 4-2F6 | 1.915 | 0.1145 | 19 | 5 |
| 4-3A7 | 0.1286 | 0.1186 | 49 | 5 |
| 4-1E2 | 0.13 | 0.3 | 53 | 24 |
| Control IgG | 0.05 | 0.05 | 8 | 5 |

ANTIGEN 4—(x=number of peptide conjugated to KLH; we also inject peptide conjugated to KLH into mice that have been pre-immunized with CR(del C)-Fc as described, e.g., in Protocol C):

Sequences of exemplary CRx peptides that we used and their positions in the full length Cripto protein are as follows:

CR40 = FRDDSIWPQEEPAIRPR
(aa46-42, A10.B2; SEQ ID NO: 3)

CR41 = CPPSFYGRNCEHDVRKE
(aa97-113; SEQ ID NO: 4)

CR43 = GSVPHDTWLPKKC
(aa116-128; SEQ ID NO: 5)

CR44 = SLCKSWHGQLRCFPQ
(aa129-143; SEQ ID NO: 6)

CR49 = acetylated
N-SFYGRNCEHDVRRENCGSVPHDTWLPKK-COO⁻
(aa100-aa127; SEQ ID NO: 7)

CR50 = acetylated
N-LNEGTCMLGSFCACPPSFYGRNCEHDVRK-COO⁻
(aa84-aa112, includes the fucosylation region;
SEQ ID NO: 8)

CR51 = acetylated
N-PHNTWLPKKCSLCKCWHGQLRCFPQAFLPGCD-COO⁻
(aa119-aa150; SEQ ID NO: 9)

| Protocol E: | |
| --- | --- |
| 1° | 50 µg CRx-KLH (IP) + FCA |
| 2° | 50 µg CRx-KLH (IP) + FIA |
| 3° | 50 µg CRx-KLH (IP) + FIA |
| 4° | 25 µg CR(del C)-Fc (IV) in PBS |

| Protocol F: | |
| --- | --- |
| 1° | 50 µg CR(del C)-Fc (IP) + FCA |
| 2° | 50 µg CR(del C)-Fc (IP) + FIA |
| 3° | 50 µg CR(del C)-Fc (IP) + FIA |
| 4° | 25 µg CRx-KLH (IP) + FIA |

Example 3

Null Cell Assay for Inhibition of Cripto Activity

The following describes an F9 Cripto null cell signaling assay used to assess inhibition of Cripto activity.

Day 0 Coat 6 welled plates with 0.1% gelatin 2 ml/well at 37° C. for 15 min.

Seed cells at $6 \times 10^5$ F9 CRIPTO NULL cells per well.

Day 1 Transfection:

Each of the following samples is added to 300 µl Opti-Mem1 to yield Solution A for each sample:

Sample 1: 0.5 µg $(N_2)_7$ luciferase FAST reporter cDNA plus 1.5 µg empty vector cDNA.

Sample 2: 0.5 µg $(N_2)_7$ luciferase, 0.5 µg FAST, and 1 µg empty vector cDNAs.

Sample 3: 0.5 µg $(N_2)_7$ luciferase, 0.5 µg Cripto ADD 0.5 FAST, and 0.5 µg empty vector cDNAs.

Sample 4: 0.5 µg $(N_2)_7$ luciferase, 0.5 µg Cripto, 0.5 FAST, and 0.5 µg empty vector cDNAs Sample 5: 0.5 µg $(N_2)_7$ luciferase, 0.5 µg Cripto, 0.5 FAST, and 0.5 µg empty vector cDNAs.

Sample 6: 0.5 µg $(N_2)_7$ luciferase, 0.5 µg Cripto, 0.5 FAST, and 0.5 µg empty vector cDNAs.

Sample 7: 0.5 µg $(N_2)_7$ luciferase, 0.5 µg Cripto, 0.5 FAST, and 0.5 µg empty vector cDNAs.

Sample 8: 0.5 µg $(N_2)_7$ luciferase, 0.5 µg Cripto, 0.5 FAST, and 0.5 µg empty vector cDNAs.

Sample 9: 0.5 µg $(N_2)_7$ luciferase, 0.5 µg Cripto, 0.5 FAST, and 0.5 µg empty vector cDNAs.

Solution B comprises 30 µl of Lipofectamine plus 270 µl of OptiMem1.

For each sample, mix solution A and solution B together. Incubate 45 minutes at room temperature. Rinse wells with 2 ml/well of OptiMem1. Aspirate just before next step.

Add 2.4 ml of OptiMem1 to each mixture of solutions A+B, mix, add 1.5 ml/well to duplicate wells. Incubate 5 hours at 37° C. Add 1.5 ml/well of DMEM+20% FCS, 2 mM Gln, P/S to wells which received samples 1-3. Add anti-Cripto antibodies as follows: Sample 4 wells: A27F6.1, 10 µg/ml; Sample 5 wells: A27F6.1, 2 µg/ml; Sample 6 wells: A40G12.8; 10 µg/ml, Sample 7 wells: A40G12.8 2 µg/ml; Sample 8 wells: A10B2.18, 10 µg/ml; Sample 9 wells: A10B2.18, 2 µg/ml.

Day 2 Remove media, wash cells with PBS, 2 ml/well. Add DMEM+0.5% FCS, 2 mM Gln, P/S with the same amounts of Cripto antibodies as the previous day, to the same wells.

Day 3 Develop luciferase signal. Wash wells with PBS+ $Ca^{2+}$ and $Mg^{2+}$, 2 ml/well. Use LucLite kit, Packard cat# 6016911. Bring buffer and substrate to room temperature. Dim lights. Reconstitute substrate with 10 ml of buffer. Dilute 1:1 with PBS+$Ca^{2+}$ and $Mg^{2+}$. Aspirate wells. Quickly add 250 µl of diluted substrate per well using a repeat pipettor. Swirl solution and transfer 200 µl to wells of a 96 welled white opaque bottom plate, Falcon 35-3296. Read plate on luminometer using Winglow, exporting data to Excel.

The results of this assay with certain of the antibodies of the invention are summarized below in Table 3.

TABLE 6

Cripto Activity Assay: Inhibition with Anti-Cripto Monoclonal Antibodies

| cDNAs transfected | Anti-Cripto Antibody | | Relative Luminescent Units |
| --- | --- | --- | --- |
| $(N_2)_7$ luc | None | | 123 |
| $(N_2)_7$ luc, FAST | None | | 259 |
| $(N_2)_7$ luc, FAST, Cripto | None | | 3091 |
| $(N_2)_7$ luc, FAST, Cripto | A27F6.1 | 10 µg/ml | 1507 |
| $(N_2)_7$ luc, FAST, Cripto | A27F6.1 | 2 µg/ml | 2297 |
| $(N_2)_7$ luc, FAST, Cripto | A40G12.8 | 10 µg/ml | 1213 |
| $(N_2)_7$ luc, FAST, Cripto | A40G12.8 | 2 µg/ml | 2626 |
| $(N_2)_7$ luc, FAST, Cripto | A10B2.18 | 10 µg/ml | 3466 |
| $(N_2)_7$ luc, FAST, Cripto | A10B2.18 | 2 µg/ml | 3103 |

We also tested other concentrations of A27F6.1 antibody. We observed that addition of 0.5-20 mg/ml mab A27F6.1 to the media of these cells inhibited the Cripto-induced luciferase signal by 34-95% (FIG. 1). We also tested other antibodies of the invention and observed that mabs A6C12.11 and A8G3.5 also inhibited signal production.

Figure 2:
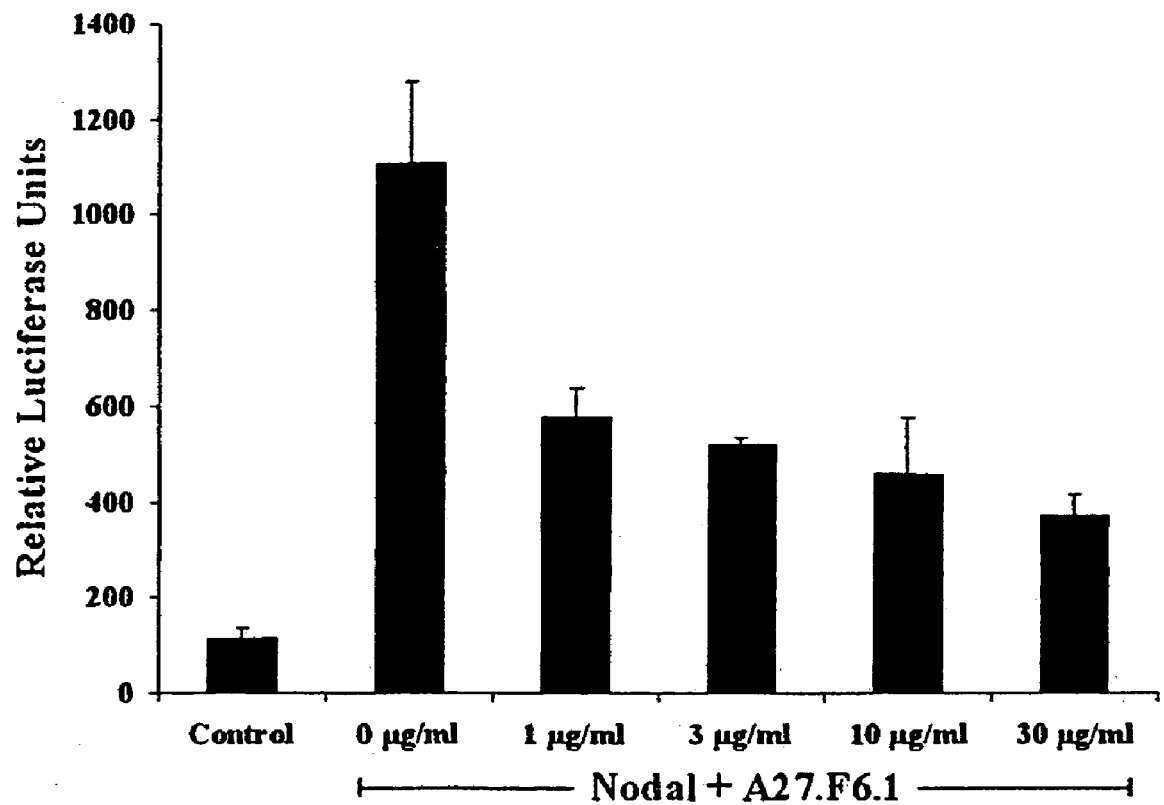
FIG. 2 depicts the response of the human testicular carcinoma cell line NCCIT to the monoclonal antibody A27F6.1, and shows that the antibody decreased luciferase activity in these cells by 90% at both 2 and 20 mg/ml.

As as alternative assay system, we tested the Cripto specific mabs of the invention for inhibition of FAST/$(N2)_7$-luc activity in NCCIT cells. These assays were similar to those for the F9 cells, except ectopic expression of Nodal and ALK4 is required in these cells for reporter activation. We observed that mab A27F6.1 decreased luciferase activity in these cells by 90% at both 2 and 20 µg/ml (FIG. 2).

Example 4

Assay for In Vitro Inhibition of Tumor Cell Growth

Inhibition of Cripto activity may also be assayed by measuring the growth of GEO cells in soft agar. See, e.g., Ciardiello et al., 1994, *Oncogene* 9:291-98; Ciardiello et al., 1991, *Cancer Res.* 51:1051-54.

We melted 3% bactoagar and kept it at 42° C. in a water bath. We mixed the 3% bactoagar solution with prewarmed complete media to make a solution of 0.6% bactoagar and kept it at 42° C. We plated 4 ml of the solution in a 6 cm dish and let it cool for at least 30 minutes to allow the bottom agar layer to form. We trypsinized GEO cells and resuspend to $10^5$ cells/ml in complete media. We added antibodies to be assayed, or controls, to the cell suspensions, titrating antibodies from 20 µg to 1 µg. We mixed equal volumes of the GEO cell suspensions and 0.6% bactoagar and overlaid 2 ml on top of the bottom agar layer. We allowed the plates to cool for at least 1 hour. We incubated for 14 days at 37° C. in $CO_2$ incubator. We counted colonies visible without the use of a microscope. The absence of colonies, as compared to negative controls, indicated that the antibody tested inhibited in vitro tumor cell growth.

This assay was used to yield the results shown in Table 4 for the antibodies A27F6.1 and B6G7.10, both of which demonstrate the ability to decrease growth of GEO cell colonies.

TABLE 7

Results of growth in soft agar assay

| Antibody | Average number of colonies |
|---|---|
| none | 109.0 |
| none | 104.3 |
| A27.F6 20 µg/ml | 82.0 |
| A27F6.1 10 µg/ml | 78.3 |
| A27F6.1 5 µg/ml | 79.0 |
| A27F6.1 1 µg/ml | 108.7 |
| B6G7.10 20 µg ml | 102.3 |
| B6G7.10 10 µg/ml | 71.7 |

We also performed growth inhibition assays with T-47D cells (ATCC) which is a non-tumorigenic human breast carcinoma as described in Example 9.

Example 5

Assay for In Vivo Inhibition of Tumor Cell Growth

To assess the inhibition of tumor cell growth, a human tumor cell line is implanted subcutaneously in athymic nude mice and the effects of the antibodies of the invention are observed, with and without additional chemotherapeutic treatments which may provide synergistic or additive effects on tumor inhibition.

This assay may be performed alternatively using different tumor cell lines, such as, for example, GEO (a well differentiated human colon cancer in vitro cell line, is obtained from the American Tissue Type Collection (ATCC)), DU-4475 (a breast cancer in vitro cell line obtained from the ATCC), NCCIT (a testicular tumor cell line obtained from ATCC), or others known in the art. One example of such assays is described below.

Animals are individually marked by ear punches. The GEO cell line is passed in vitro or in vivo for 1-4 passages. Animals are implanted with GEO cells subcutaneously in the right flank area. The following groups of animals may be used:

| Group # | Treatment | # of Mice |
|---|---|---|
| 1. | Saline Control, 0.2 ml/mouse, i.p. three times weekly (M, W, F) | 20 |
| 2. | Mab, low dose, i.p. | 10 |
| 3. | Mab, middle dose, i.p. | 10 |
| 4. | Mab, high dose, i.p. | 10 |
| 5. | 5-FU, 30 mg/kg/inj, i.p., 3 Rx/wk (M, W, F) | 10 |
| 6. | Cisplatin, 2 mg/kg/inj, s.c., 3 Rx/wk (M, W, F) | 10 |
| 7. | Adriamycin, 1.6 mg/kg/inj, i.p., 3 Rx/wk (M, W, F) | 10 |
| 8. | Irinotecan, 10 mg/kg/inj., i.p., 5 Rx/wk (M-F) | 10 |
| 9. | MAb, low dose, i.p. + 5-FU (intermediate dose) | 10 |
| 10. | MAb, middle dose, i.p. + 5-FU (intermediate dose) | 10 |
| 11. | MAb, high dose, i.p. + 5-FU (intermediate dose) | 10 |
| 12. | MAb, low dose, i.p. + Cisplatin (intermediate dose) | 10 |
| 13. | MAb, middle dose, i.p. + Cisplatin (intermediate dose) | 10 |
| 14. | MAb, high dose, i.p. + Cisplatin (intermediate dose) | 10 |
| 15. | MAb, low dose, i.p. + Adriamycin (intermediate dose) | 10 |
| 16. | MAb, middle dose, i.p. + Adriamycin (intermediate dose) | 10 |
| 17. | MAb, high dose, i.p. + Adriamycin (intermediate dose) | 10 |
| 18. | MAb, low dose, i.p. + Irinotecan (intermediate dose) | 10 |
| 19. | MAb, middle dose, i.p. + Irinotecan (intermediate dose) | 10 |
| 20. | MAb, high dose, i.p. + Irinotecan (intermediate dose) | 10 |

Day 0: Implant tumor, record initial body weight of animals.

Day 1: Initiate treatments as indicated above.

Day 5: Begin tumor size and body weight measurements and continue two times weekly until termination of experiment.

Initial body weight, tumor size and body weight measurements, histology at sacrifice, and immunohistochemistry analysis on tumors are examined for Cripto expression, tumor growth, and inhibition thereof.

Example 6

In Vivo Xenograft Tumor Model—Cys-rich Blocking Anti-Cripto Antibody

Figure 3:
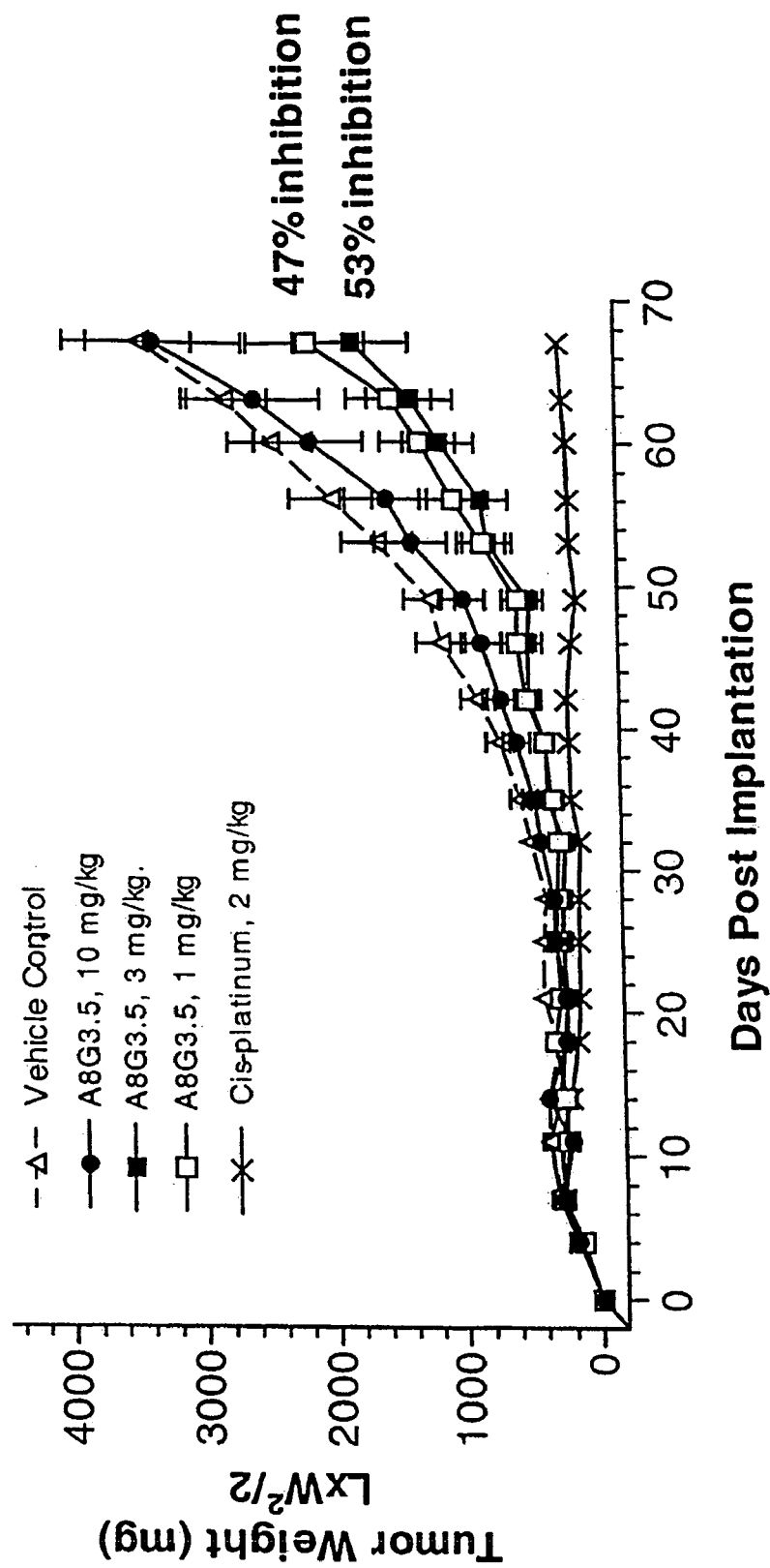
FIG. 3 illustrates depicts the response of NCCIT, a human testicular carcinoma cell line implanted simultaneously with an antibody which binds to the cys-rich domain of Cripto.

To assess the response of an NCCIT, a human testicular carcinoma cell line was implanted subcutaneously with an antibody which binds to a cys-rich domain of Cripto. The experimental methods are listed below. The results are shown in FIG. 3.

Methods and Materials

Animals: Athymic nude male mice were used. Animals were individually numbered by ear punches.

Tumor: NCCIT, mediastinal mixed germ cell human testicular carcinoma in-vitro cell line originally obtained from the American Tissue Type Collection. Cell line was passed in vitro for six passages in RPMI-1640/10% FBS without antibiotics. Animals implanted subcutaneously with $5\times10^6$ cells/0.2 ml matrigel on the animals right flank.

| Group # | Treatment | # of Mice |
|---|---|---|
| 1 | Vehicle Control (25 mM sodium phosphate, 100 mM sodium chloride, pH 7.2), 0.2 ml/mouse, i.p., Q14D Treatments begin on day - 1 | 20 |
| 2. | A8G3.5, 1 mg/kg/inj, i.p., Q14D Treatments begin on day - 1 | 10 |
| 3. | A8G3.5, 3 mg/kg/inj, i.p., Q14D Treatments begin on day - 1 | 10 |
| 4. | A8G3.5, 10 mg/kg/inj, i.p., Q14D Treatments begin on day - 1 | 10 |
| 5. | Cis-platinum, 2 mg/kg/inj, s.c., 3x/wk (M, W, F) for 6 treatments | 10 |

Treatments began on day 1.

Testing Schedule

Day −1: Randomized mice into control and treatments groups. Recorded initial body weight of animals. Administered first treatments to antibody groups. Dosing solutions were made. Treatments were blinded to the technicians until the assay was terminated.

Day 0: Implanted tumor. Ran bacterial cultures on the tumor implanted into mice.

Day 1: Administered first treatment to the positive chemotherapeutic group.

Day 4: Recorded initial tumor size measurements for tumor baseline on matrigel. Continued to record tumor size and body-weights on mice 2x/week. Monitored the study daily and made notations of any unusual observation on animals.

Endpoints: Initial body weight
Tumor size and body weight measurements

Example 7

In Vivo Xenograft Tumor Model—EGF-like Domain Blocking Anti-Cripto Antibody

Figure 4:
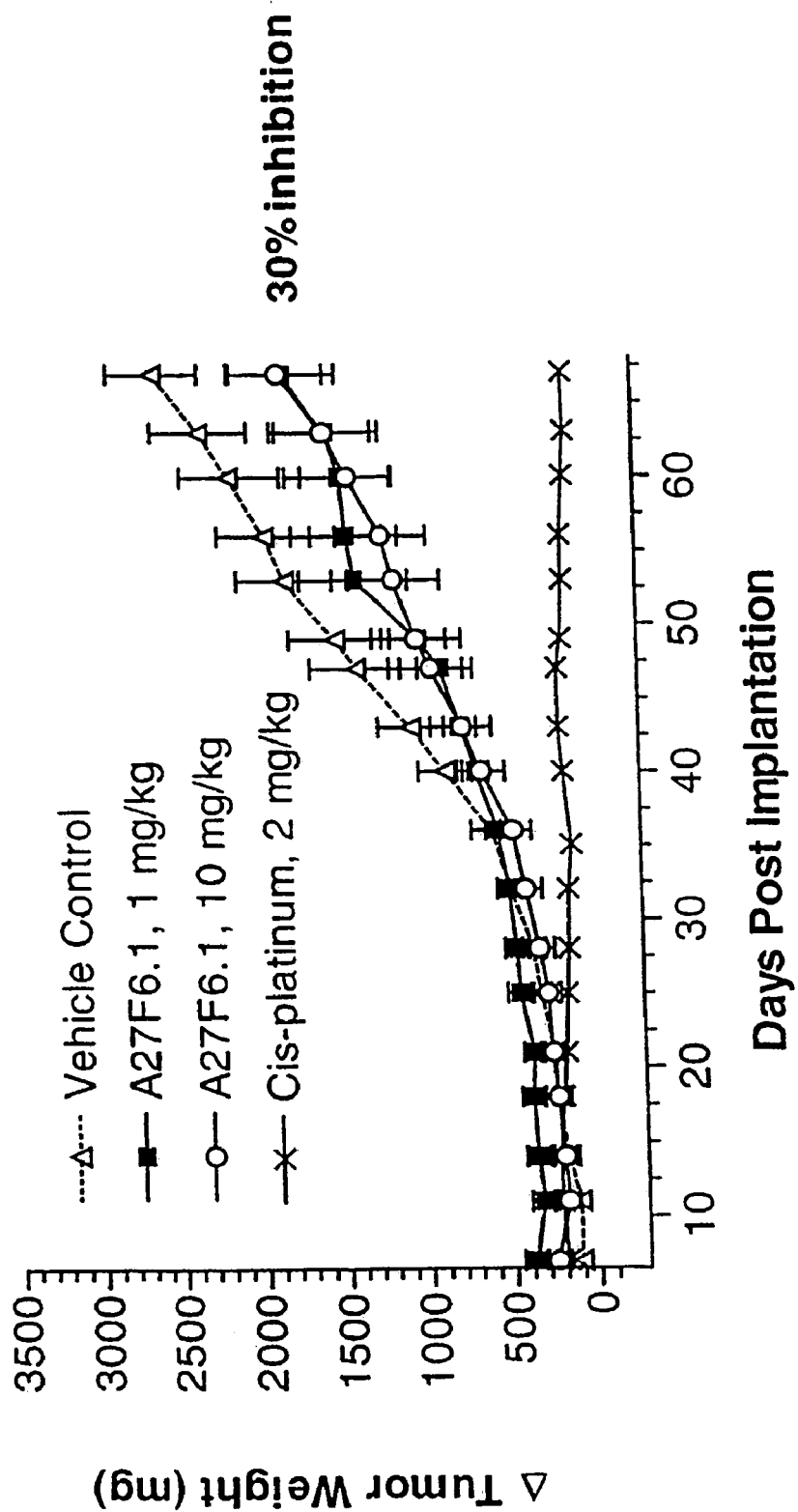
FIG. 4 illustrates depicts the response of NCCIT, a human testicular carcinoma cell line implanted simultaneously with an antibody which binds to an EGF-like domain of Cripto.
Figure 5:
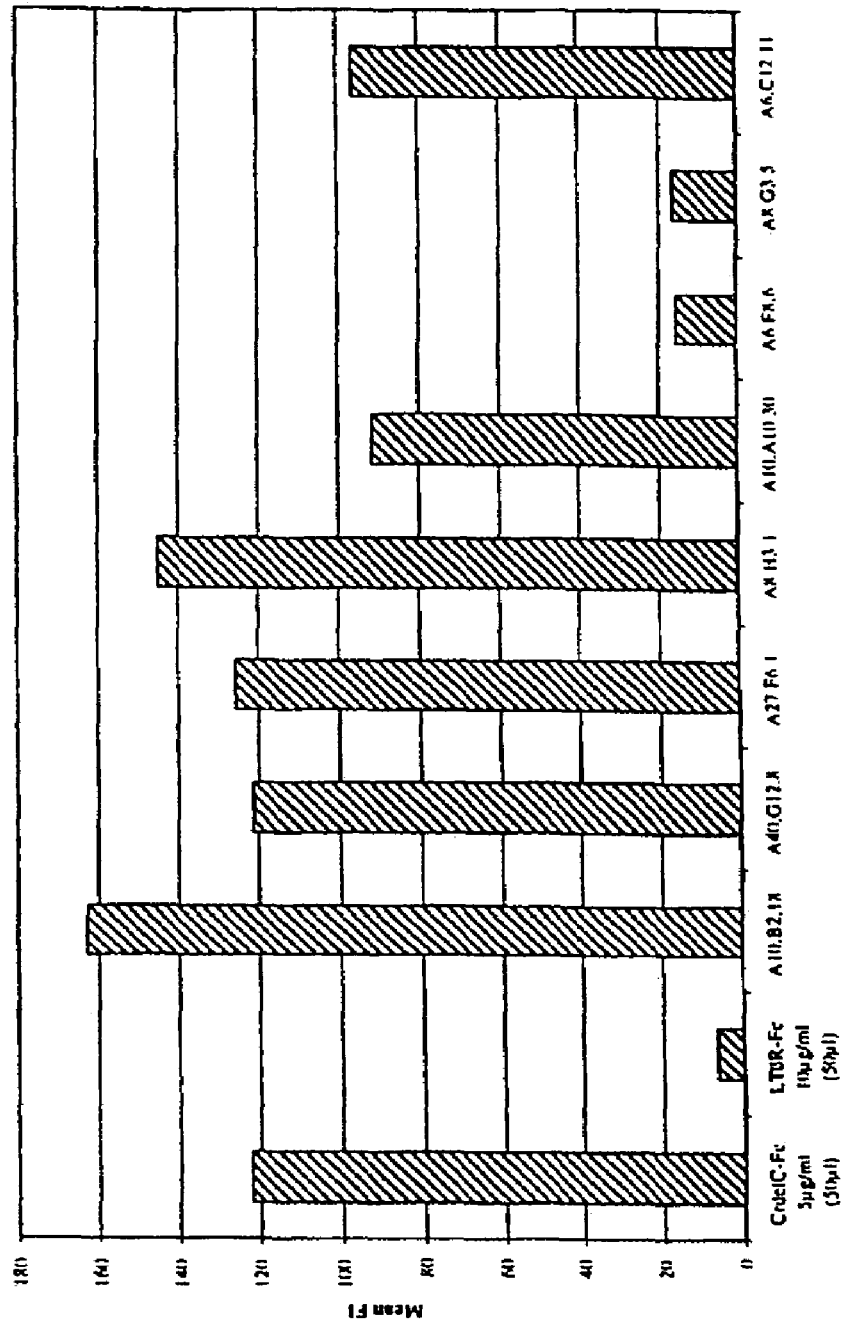
FIG. 5 shows the results of an analysis of Cripto-ALK4 binding by flow cytometry in which a purified, soluble form of human Cripto (aa 1-169) fused to the Fc portion of human IgG (CR(delC)-Fc) was employed.

To assess the response of an NCCIT, a human testicular carcinoma cell line was implanted subcutaneously with an antibody which binds to a EGF-like domain of Cripto. The experimental methods are listed below. The results are shown in FIG. 4.

Methods and Materials

Animals: Athymic nude male mice were used. Animals were individually numbered by ear punches.

Tumor: NCCIT, mediastinal mixed germ cell human testicular carcinoma in vitro cell line originally obtained from the American Tissue Type Collection. Cell line was passed in vitro for eight passages in RPMI-1640/10% FBS without antibiotics. Animals implanted subcutaneously with $5\times10^6$ cells/0.2 ml matrigel on the animals right flank.

| Group # | Treatment | # of Mice |
|---|---|---|
| 1. | Vehicle Control, (25 mM sodium phosphate, 100 mM sodium chloride, pH 7.2), 0.2 ml/mouse, i.p., Q14D Treatments begin on day - 1 | 18 |
| 2. | A27F6.1, 1 mg/kg/inj, i.p., Q14D Treatments begin on day - 1 with a loading dose of 2.6 mg/kg/mouse | 10 |
| 3. | A27F6.1, 10 mg/kg/inj, i.p., Q14D Treatments begin on day - 1 with a loading dose of 21.2 mg/kg/mouse | 10 |
| 4. | Cis-platinum, 2 mg/kg/inj, s.c., 3x/wk (M, W, F) for 6 treatments | 10 |

Treatments began on day 1.

Testing Schedule

Day −1: Randomized mice into control and treatments groups. Recorded initial body weight of animals. Administered first treatments to antibody groups. Dosing solutions were made. Treatments were blinded to the technicians until the assay was terminated.

Day 0: Implant tumor. Ran bacterial cultures on the tumors implanted into mice. Bacterial culture were negative for contamination at 24 and 48 hours post sampling.

Day 1: Administered first treatment to the positive chemotherapeutic group.

Day 4: Recorded initial tumor size measurements for tumor baseline on matrigel. Continued to record tumor size and body weights on mice 2x/week. Monitored the study daily and made notations of any unusual observation on animals.

Endpoints: Initial Body Weight
Tumor size and body weight measurements

Example 8

Cripto mabs Modulate ALK4 Binding

In order to assess whether Cripto-specific monoclonal antibodies can interfere with Cripto's ability to bind to ALK4, the activin type I receptor, we used flow cytometry analysis using a 293 cell line which stably expresses ALK4. To generate this cell line, 293 cells were cotransfected with a plasmid that expresses ALK4 tagged at the C-terminus with a HA epitope and a plasmid that expresses puromycin at a 10:1 ratio. The transfected cells were then selected in puromycin until colonies formed. Colonies were then picked, expanded and analyzed for ALK4 expression using western blotting analysis for HA. Clone 21 (293-Alk4-21) was found to express high levels of ALK4 compared to control, untransfected 293 cells.

To analyze Cripto-ALK4 binding by flow cytometry, a purified, soluble form of human Cripto (aa 1-169) fused to the Fc portion of human IgG (CR(delC)-Fc) was employed. Approximately 5 µg/ml of CR(delC)-Fc or control Fc protein was incubated with $3\times10^5$ 293-Alk4-21 cells on ice for 30 minutes in 50 µl total volume of FACS buffer (PBS with 0.1% BSA). For samples containing anti-Cripto antibodies, 5 µg/ml CrdelC-Fc was preincubated with 50 µg/ml of each Cripto antibody (A10.B2.18, A40.G12.8, A27.F6.1, A8.H3.1, A19.A10.30, A6.F8.6, A8.G3.5, A6.C12.11) on ice prior to addition of the cells. The cells were then washed in FACS buffer and the bound Fc protein was detected by incubating the cells with a R-phycoerytherin-conjugated goat anti-human IgG (Fc fragment specific) from Jackson Immunologics. Samples were then washed again, fixed in 1% paraformaldehyde in PBS, and analyzed using standard flow cytometry procedures. The results of the FACS assay are shown in FIG. 5.

Example 9

Cripto Disrupts Activin B-Induced Growth Suppression of Breast Cancer Cells T47D cells, maintained in RPMI/10% FCS/10 μg/ml insulin, at passage #2 from the ATCC were transfected with an expression plasmid for the Ecotropic Receptor (EcoR; B. Elenbaas) and selected in media containing 100 μg/ml hygromycin. Colonies of T-47D-EcoR that permitted infection of pBABE-GFP murine leukemia virus (MLV) were grown out, infected with pBABE-hCr-PURO-MLV and selected in puromycin media. This oligoclonal line (T-47D-hCr) was analyzed by FACS for hCr (human Cripto) expression with specific anti-Cripto antibodies. Approximately 4000 cells/well of T-47D-EcoR or T-47D-hCr were plated in a 96 well plate in media containing 2% serum with/without 25 ng/ml Activin B (R&D) or ng/ml Activin B plus 0.1-50 μg/ml A8G3.5. Media with factors was replaced daily for 7-8 days. The plate was harvested by adding 20 μl/well CellTiter AQ$_{ueous}$ One solution (Promega), incubating 2 hours 37° C., and reading at 490 nm.

Figure 6:
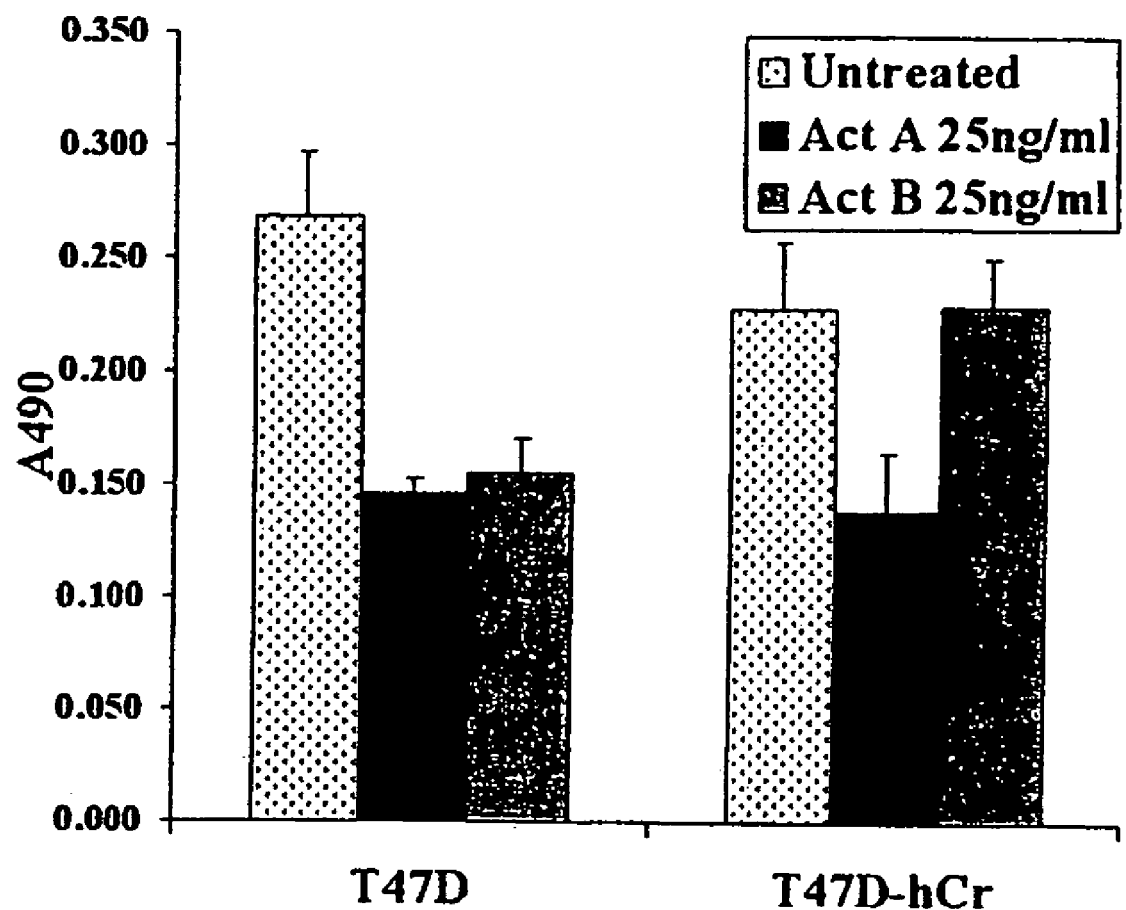
FIG. 6 illustrates that proliferation of T-47D cells was inhibited by Activin A or B by approximately 40% compared to untreated cells. In addition, the FIG. shows that the T-47D-CR cells were not responsive to Activin B.

We grew T-47D and T-47D-EcoR cells in low serum conditions, with or without Activin A or B and assayed for proliferating cells using an MTT colorimetric assay. We observed that proliferation of T-47D cells was inhibited by Activin A or B by approximately 40% compared to untreated cells (FIG. 6). We also observed that T-47D-CR cells were inhibited by Activin A, but discovered that the T-47D-CR cells were not responsive to Activin B (FIG. 6). This result indicates that Cripto's effect on proliferation of these cells is specific to Activin B. We observed in control experiments that untreated T-47D and T-47D-CR cells did not differ in proliferation rates in either normal media or in low serum conditions.

Figure 7:
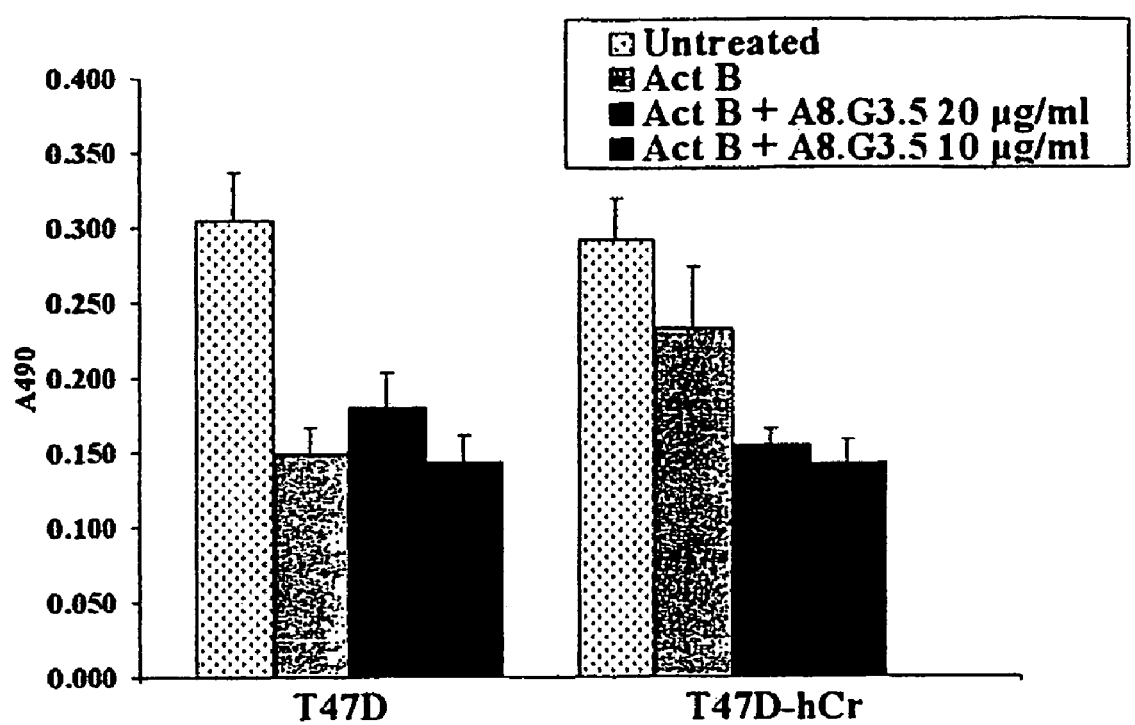
FIG. 7 shows that antibodies can inhibit the Cripto-Activin B interaction. Briefly, T-47D-CR cells were treated with Activin B in the presence of various antibodies. Growth suppressive activity of Activin B was restored in the presence of 10 or 20 µg/ml mab A8G3.5. In addition, the A27F6.1 mab was unable to restore Activin B growth suppression of these cells.

We then tested whether antibodies of the invention can inhibit the Cripto-Activin B interaction. We treated T-47D-CR cells with Activin B in the presence of various antibodies of the invention. We observed that the growth suppressive activity of Activin B was restored in the presence of 10 or 20 μg/ml mab A8G3.5 (FIG. 7). We observed that the A27F6.1 mab was unable to restore Activin B growth suppression of these cells.

Example 10

Cripto Binds Directly to Activin B

Figure 8:
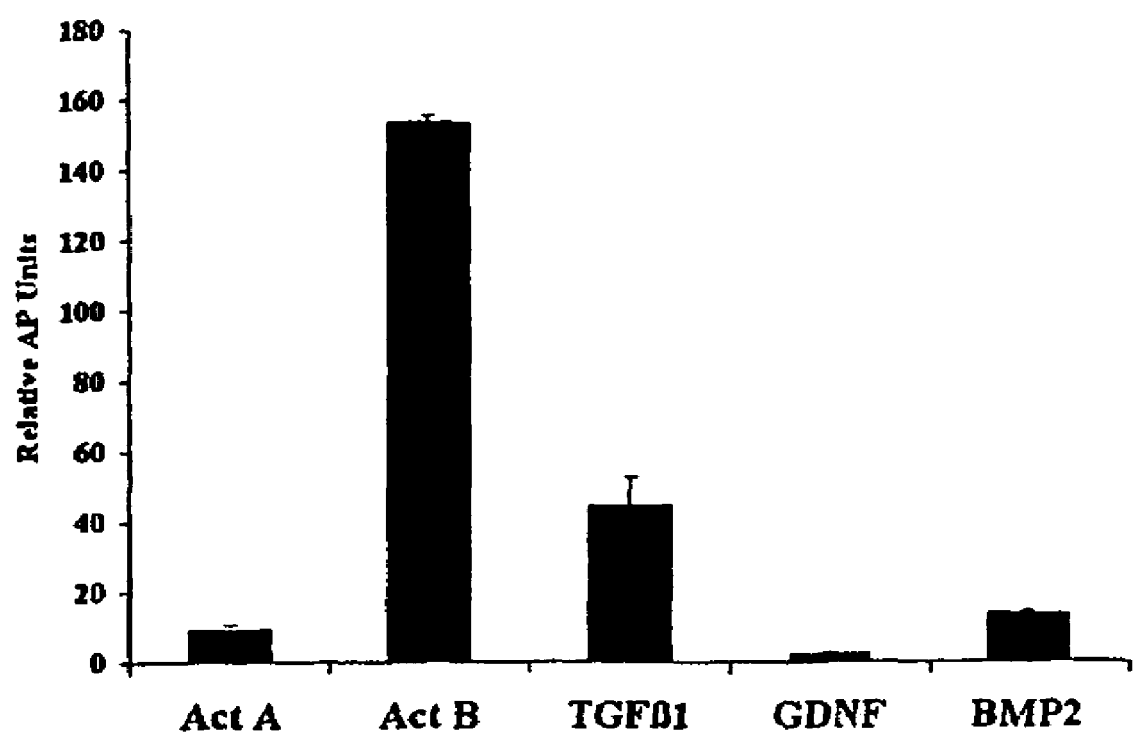
FIG. 8 shows that CR-Fc bound to wells containing Activin B, but not to Activin A or the other ligands
Figure 9:
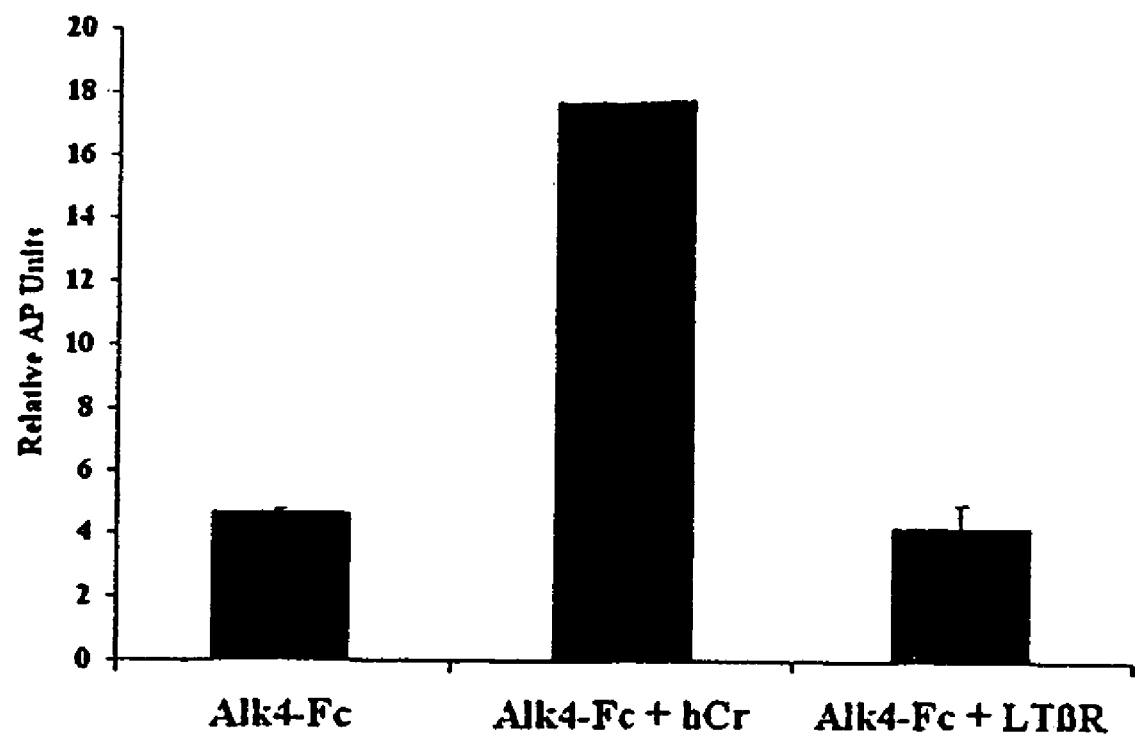
FIG. 9 shows that when CR-Fc is preincubated with Activin A or B in solution before adding to an Activin B coated plate, only Activin B inhibits binding.

We discovered that Cripto binds directly to Activin B. We coated ELISA plates with purified Activin B, Activin A, TGFβ1, GDNF or BMP2 and incubated with CR-Fc. We then added anti-Fc antibody conjugated to alkaline phosphatase and monitored binding by adding an alkaline phosphatase substrate and developing. We observed that CR-Fc bound to wells containing Activin B, but not to Activin A or the other ligands (FIG. 8). In addition, we pre-incubated CR-Fc with Activin A or B in solution before adding to an Activin B coated plate and observed that only Activin B inhibited binding (FIG. 9). These results confirmed that Cripto specifically binds Activin B.

Figure 10:
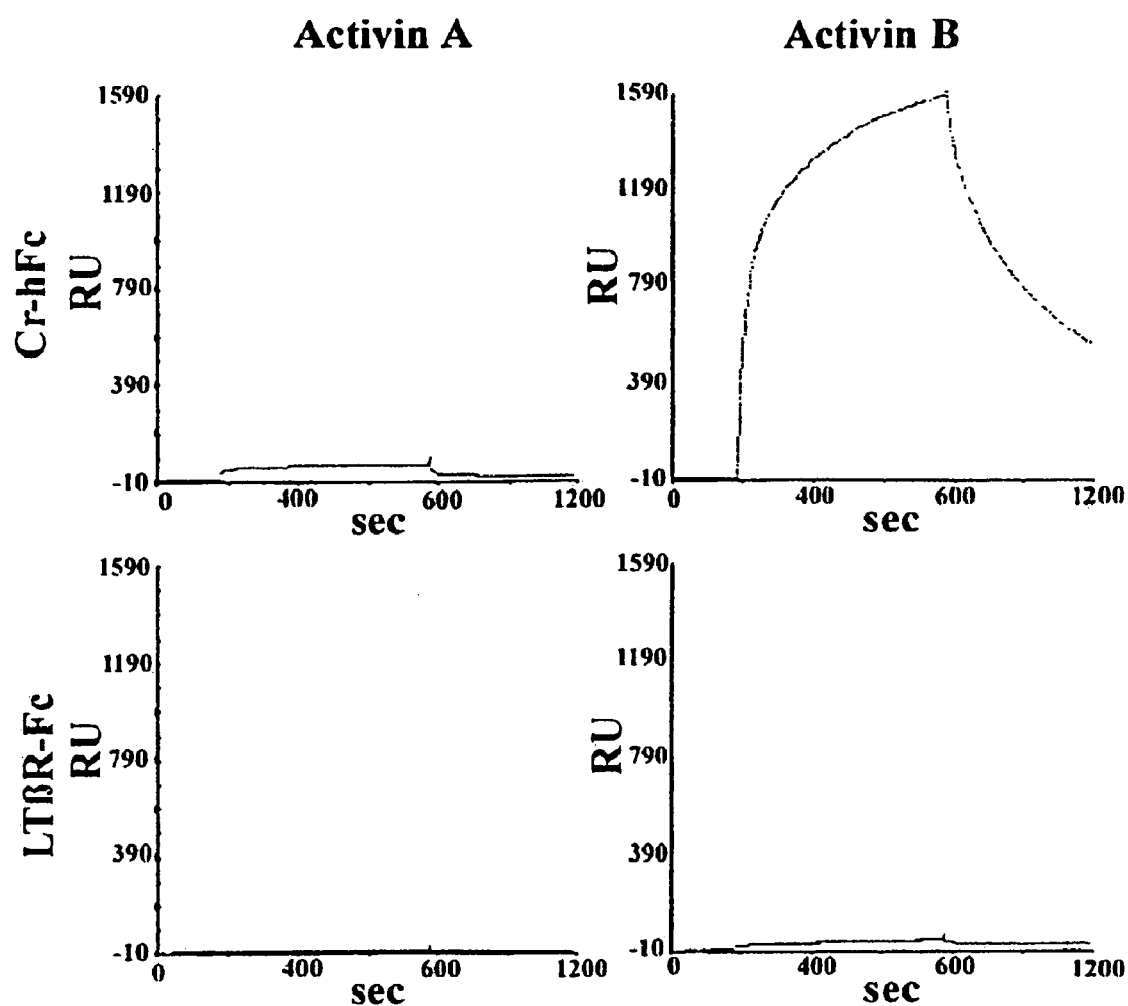
FIG. 10 shows the Cripto-Activin B interaction using Biacore. Activin B directly binds CR-Fc immobilized on a Biacore chip with a high intensity, but not to a control LTβR-Fc protein.

We also analyzed the Cripto-Activin B interaction using Biacore. We discovered that Activin B directly binds CR-Fc immobilized on a Biacore chip with a high intensity, but not to a control LTβR-Fc protein (FIG. 10). We also observed that Activin A binding to CR-Fc was negligible. These data indicate that Activin B binds Cripto with a fast on rate and an apparent affinity in solution measured a competition format assay of about 1 nM.

Cripto anti-CFC monoclonal antibodies 2-2C9.2 and A8G3 modulated the interaction of Cripto with Activin B. This was shown by coimmunoprecipitation experiments in which Cripto binding to Activin B was inhibited by addition of A8G3 or 2-2C9.2. The inhibition was measured using conventional western blotting techniques with anti-Activin B antibodies.

Some of the embodiments of the invention described above are outlined below and include, but are not limited to, the following embodiments. As those skilled in the art will appreciate, numerous changes and modifications may be made to the various embodiments of the invention without departing from the spirit of the invention. It is intended that all such variations fall within the scope of the invention.

The entire disclosure of each publication cited herein is hereby incorporated by reference.

What is claimed is:

1. A method of inhibiting angiogenesis of tumor cells in vivo comprising administering an antibody that specifically binds to an epitope comprised in the cysteine-rich domain of Cripto spanning from amino acid residue 114 to amino acid residue 150 of SEQ ID NO:1 or amino acid residue 114 to amino acid residue 150 of SEQ ID NO:2, wherein the antibody blocks the interaction of Cripto with Activin B and/or Alk4, to a subject having a tumor in an amount sufficient to inhibit angiogenesis such that angiogenesis is inhibited.

2. The method of claim 1, wherein the antibody is an antibody fragment selected from the group consisting of a Fab, a Fab', and a F(ab')2 fragment.

3. The method of claim 1, wherein the antibody is a full length antibody.

4. The method of claim 1, wherein the antibody is a single chain antibody.

5. The method of claim 1, wherein the antibody is conjugated to a chemotherapeutic agent.

6. The method of claim 1, wherein the antibody is administered in combination with a nonconjugated chemotherapeutic.

7. The method of claim 5 or 6, wherein the chemotherapeutic agent is selected from the group consisting of a tumor-activated prodrug, a radionuclide and a toxin.

8. The method of claim 7, wherein the chemotherapeutic agent is a tumor-activated prodrug.

9. The method of claim 8, wherein the tumor-activated prodrug is a maytansinoid.

10. The method of claim 1, wherein the antibody is human.

11. The method of claim 1, wherein the antibody is monoclonal.

12. The method of claim 1, wherein the antibody is humanized.

13. The method of claim 1, wherein the antibody is a humanized version of the A8.G3.5 antibody or an antigen binding fragment thereof.

14. The method of claim 1, wherein the antibody is a humanized version of an antibody selected from the group consisting of: the A8.G3.5 antibody, A6F8.6; 1-1A4C.2; and 2-2C9.2 or an antigen binding fragment thereof.

15. The method of claim 1, wherein the antibody blocks the interaction of Cripto and Alk4.

16. The method of claim 1, wherein the antibody blocks the interaction of Cripto and Activin B.

17. A method of inhibiting the growth of tumor cells in vivo comprising administering an antibody that specifically binds to an epitope comprised in the cysteine-rich domain of Cripto spanning from amino acid residue 114 to amino acid residue 150 of SEQ ID NO:1 or amino acid residue 114 to amino acid residue 150 of SEQ ID NO:2, wherein the antibody blocks the interaction of Cripto with Activin B and/or Alk4, to a subject having a tumor.

18. The method of claim 17, wherein the antibody is an antibody fragment selected from the group consisting of a Fab, a Fab', and a F(ab')2 fragment.

19. The method of claim 17, wherein the antibody is a full length antibody.

20. The method of claim 17, wherein the antibody is a single chain antibody.

21. The method of claim 17, wherein the antibody is conjugated to a chemotherapeutic agent.

22. The method of claim 17, wherein the antibody is administered in combination with a nonconjugated chemotherapeutic.

23. The method of claim 20 or 21, wherein the chemotherapeutic agent is selected from the group consisting of a tumor-activated prodrug, a radionuclide and a toxin.

24. The method of claim 22, wherein the chemotherapeutic agent is a tumor-activated prodrug.

25. The method of claim 23, wherein the tumor-activated prodrug is a maytansinoid.

26. The method of claim 17, wherein the antibody is human.

27. The method of claim 17, wherein the antibody is monoclonal.

28. The method of claim 17, wherein the antibody is humanized.

29. The method of claim 17, wherein the antibody is a humanized version of the A8.G3.5 antibody or an antigen binding fragment thereof.

30. The method of claim 17, wherein the antibody is a humanized version of an antibody selected from the group consisting of: the A8.G3.5 antibody, A6F8.6; 1-1A4C.2; and 2-2C9.2 or an antigen binding fragment thereof.

31. The method of claim 17, wherein the antibody blocks the interaction of Cripto and Alk4.

32. The method of claim 17, wherein the antibody blocks the interaction of Cripto and Activin B.

* * * * *

UNITED STATES PATENT AND TRADEMARK OFFICE
CERTIFICATE OF CORRECTION

PATENT NO. : 7,582,299 B2
APPLICATION NO. : 10/945853
DATED : September 1, 2009
INVENTOR(S) : Sanicola-Nadel et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 501 days.

Signed and Sealed this
Twenty-third Day of October, 2012

David J. Kappos
*Director of the United States Patent and Trademark Office*

SEQUENCE LISTING

```
<160> NUMBER OF SEQ ID NOS: 9

<210> SEQ ID NO 1
<211> LENGTH: 188
<212> TYPE: PRT
<213> ORGANISM: Homo sapiens

<400> SEQUENCE: 1

Met Asp Cys Arg Lys Met Ala Arg Phe Ser Tyr Ser Val Ile Trp Ile
1               5                   10                  15

Met Ala Ile Ser Lys Val Phe Glu Leu Gly Leu Val Ala Gly Leu Gly
            20                  25                  30

His Gln Glu Phe Ala Arg Pro Ser Arg Gly Tyr Leu Ala Phe Arg Asp
        35                  40                  45

Asp Ser Ile Trp Pro Gln Glu Glu Pro Ala Ile Arg Pro Arg Ser Ser
    50                  55                  60
```

```
Gln Arg Val Pro Pro Met Gly Ile Gln His Ser Lys Glu Leu Asn Arg
 65                  70                  75                  80

Thr Cys Cys Leu Asn Gly Gly Thr Cys Met Leu Gly Ser Phe Cys Ala
                 85                  90                  95

Cys Pro Pro Ser Phe Tyr Gly Arg Asn Cys Glu His Asp Val Arg Lys
                100                 105                 110

Glu Asn Cys Gly Ser Val Pro His Asp Thr Trp Leu Pro Lys Lys Cys
            115                 120                 125

Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
                165                 170                 175

Leu Val Gly Ile Cys Leu Ser Ile Gln Ser Tyr Tyr
                180                 185

<210> SEQ ID NO 2
<211> LENGTH: 188
<212> TYPE: PRT
<213> ORGANISM: Homo sapiens

<400> SEQUENCE: 2

Met Asp Cys Arg Lys Met Val Arg Phe Ser Tyr Ser Val Ile Trp Ile
  1               5                  10                  15

Met Ala Ile Ser Lys Ala Phe Glu Leu Gly Leu Val Ala Gly Leu Gly
                 20                  25                  30

His Gln Glu Phe Ala Arg Pro Ser Arg Gly Asp Leu Ala Phe Arg Asp
             35                  40                  45

Asp Ser Ile Trp Pro Gln Glu Glu Pro Ala Ile Arg Pro Arg Ser Ser
     50                  55                  60

Gln Arg Val Leu Pro Met Gly Ile Gln His Ser Lys Glu Leu Asn Arg
 65                  70                  75                  80

Thr Cys Cys Leu Asn Gly Gly Thr Cys Met Leu Gly Ser Phe Cys Ala
                 85                  90                  95

Cys Pro Pro Ser Phe Tyr Gly Arg Asn Cys Glu His Asp Val Arg Lys
                100                 105                 110

Glu Asn Cys Gly Ser Val Pro His Asp Thr Trp Leu Pro Lys Lys Cys
            115                 120                 125

Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
                165                 170                 175

Leu Ala Gly Ile Cys Leu Ser Ile Gln Ser Tyr Tyr
                180                 185

<210> SEQ ID NO 3
<211> LENGTH: 17
<212> TYPE: PRT
<213> ORGANISM: Homo sapiens

<400> SEQUENCE: 3

Phe Arg Asp Asp Ser Ile Trp Pro Gln Glu Glu Pro Ala Ile Arg Pro
  1               5                  10                  15
```

```
Arg

<210> SEQ ID NO 4
<211> LENGTH: 17
<212> TYPE: PRT
<213> ORGANISM: Homo sapiens

<400> SEQUENCE: 4

Cys Pro Pro Ser Phe Tyr Gly Arg Asn Cys Glu His Asp Val Arg Lys
1               5                   10                  15

Glu

<210> SEQ ID NO 5
<211> LENGTH: 13
<212> TYPE: PRT
<213> ORGANISM: Homo sapiens

<400> SEQUENCE: 5

Gly Ser Val Pro His Asp Thr Trp Leu Pro Lys Lys Cys
1               5                   10

<210> SEQ ID NO 6
<211> LENGTH: 15
<212> TYPE: PRT
<213> ORGANISM: Homo sapiens

<400> SEQUENCE: 6

Ser Leu Cys Lys Cys Trp His Gly Gln Leu Arg Cys Phe Pro Gln
1               5                   10                  15

<210> SEQ ID NO 7
<211> LENGTH: 28
<212> TYPE: PRT
<213> ORGANISM: Homo sapiens
<220> FEATURE:
<221> NAME/KEY: Mod_res
<222> LOCATION: 1
<223> OTHER INFORMATION: N-terminal acetylation

<400> SEQUENCE: 7

Ser Phe Tyr Gly Arg Asn Cys Glu His Asp Val Arg Arg Glu Asn Cys
1               5                   10                  15

Gly Ser Val Pro His Asp Thr Trp Leu Pro Lys Lys
            20                  25

<210> SEQ ID NO 8
<211> LENGTH: 29
<212> TYPE: PRT
<213> ORGANISM: Homo sapiens
<220> FEATURE:
<221> NAME/KEY: Mod_res
<222> LOCATION: 1
<223> OTHER INFORMATION: N-terminal acetylation

<400> SEQUENCE: 8

Leu Asn Glu Gly Thr Cys Met Leu Gly Ser Phe Cys Ala Cys Pro Pro
1               5                   10                  15

Ser Phe Tyr Gly Arg Asn Cys Glu His Asp Val Arg Lys
            20                  25

<210> SEQ ID NO 9
<211> LENGTH: 32
<212> TYPE: PRT
<213> ORGANISM: Homo sapiens
```

```
-continued

<220> FEATURE:
<221> NAME/KEY: Mod_res
<222> LOCATION: 1
<223> OTHER INFORMATION: N-terminal acetylation

<400> SEQUENCE: 9

Pro His Asn Thr Trp Leu Pro Lys Lys Cys Ser Leu Cys Lys Cys Trp
1               5                   10                  15

His Gly Gln Leu Arg Cys Phe Pro Gln Ala Phe Leu Pro Gly Cys Asp
            20                  25                  30
```